(12) United States Patent
Loushin et al.

(10) Patent No.: US 8,032,222 B2
(45) Date of Patent: Oct. 4, 2011

(54) DEVICE FOR ELECTRICALLY AND MECHANICALLY STIMULATING A COMPARTMENT IN A BODY

(76) Inventors: Michael K. H. Loushin, Shoreview, MN (US); Keith J. Leland, Medina, MN (US); Jaydeep Yeshwant Kokate, Plymouth, MN (US)

( * ) Notice: Subject to any disclaimer, the term of this patent is extended or adjusted under 35 U.S.C. 154(b) by 531 days.

(21) Appl. No.: 12/141,675

(22) Filed: Jun. 18, 2008

(65) Prior Publication Data

US 2008/0319504 A1 Dec. 25, 2008

Related U.S. Application Data

(60) Provisional application No. 60/944,844, filed on Jun. 19, 2007.

(51) Int. Cl.
*A61N 1/00* (2006.01)
(52) U.S. Cl. .......................................................... 607/40
(58) Field of Classification Search .................... 607/40, 607/41; 606/40, 41
See application file for complete search history.

(56) References Cited

U.S. PATENT DOCUMENTS

| | | | |
|---|---|---|---|
| 3,411,507 A | 11/1968 | Wingrove | |
| 3,911,930 A | 10/1975 | Hagfors et al. | |
| 4,329,994 A | 5/1982 | Cooper | |
| 5,292,344 A | 3/1994 | Douglas | |
| 5,690,691 A | 11/1997 | Chen et al. | |
| 5,861,014 A | 1/1999 | Familoni | |
| 5,995,872 A | 11/1999 | Bourgeois | |
| 6,115,635 A | 9/2000 | Bourgeois | |
| 6,425,877 B1 | 7/2002 | Edwards | |
| 6,477,423 B1 | 11/2002 | Jenkins | |
| 6,491,663 B1 | 12/2002 | Lemelson | |
| 6,500,174 B1 * | 12/2002 | Maguire et al. | 606/41 |
| 6,832,114 B1 | 12/2004 | Whitehurst et al. | |
| 6,865,416 B2 | 3/2005 | Dev et al. | |
| 6,895,279 B2 | 5/2005 | Loeb et al. | |
| 7,150,745 B2 | 12/2006 | Stern et al. | |
| 2002/0188289 A1 * | 12/2002 | Hegde | 606/41 |
| 2003/0055465 A1 | 3/2003 | Ben-Haim et al. | |
| 2005/0096514 A1 | 5/2005 | Starkebaum | |
| 2005/0124920 A1 | 6/2005 | Gregersen | |
| 2005/0149142 A1 | 7/2005 | Starkebaum | |

(Continued)

OTHER PUBLICATIONS

Search Report and Written Opinion dated Jan. 15, 2009 from International application No. PCT/US2008/007614, filed Jun. 19, 2008.

*Primary Examiner* — George Manuel
(74) *Attorney, Agent, or Firm* — Leanne Taveggia Farrell; Westman, Champlin & Kelly, P.A.

(57) ABSTRACT

A device is provided for stimulating select body tissues and organs from within a compartment in a body. The device includes a tube having a distal end, a proximal end and a plurality of lumens. At least one distendable element is located along and coupled to the tube in closer proximity to the distal end than to the proximal end. Each distendable element is configured to expand against the compartment into a first position and contract within the compartment into a second position. At least one electrical component is in association with each of the distendable elements and configured to activate and deactivate electrical stimulation to the select body tissues and organs. The expansion and contraction of each distendable element and the activation and deactivation of each electrical component in the compartment is repeated over a period of time.

26 Claims, 18 Drawing Sheets

U.S. PATENT DOCUMENTS

| | | |
|---|---|---|
| 2005/0222638 A1 | 10/2005 | Foley et al. |
| 2005/0240239 A1 | 10/2005 | Boveja et al. |
| 2006/0069413 A1 | 3/2006 | Imran |
| 2007/0016262 A1 | 1/2007 | Gross et al. |
| 2007/0250020 A1 | 10/2007 | Kim et al. |
| 2007/0293885 A1 | 12/2007 | Binmoeller |
| 2008/0097468 A1* | 4/2008 | Adams et al. ........... 606/119 |

* cited by examiner

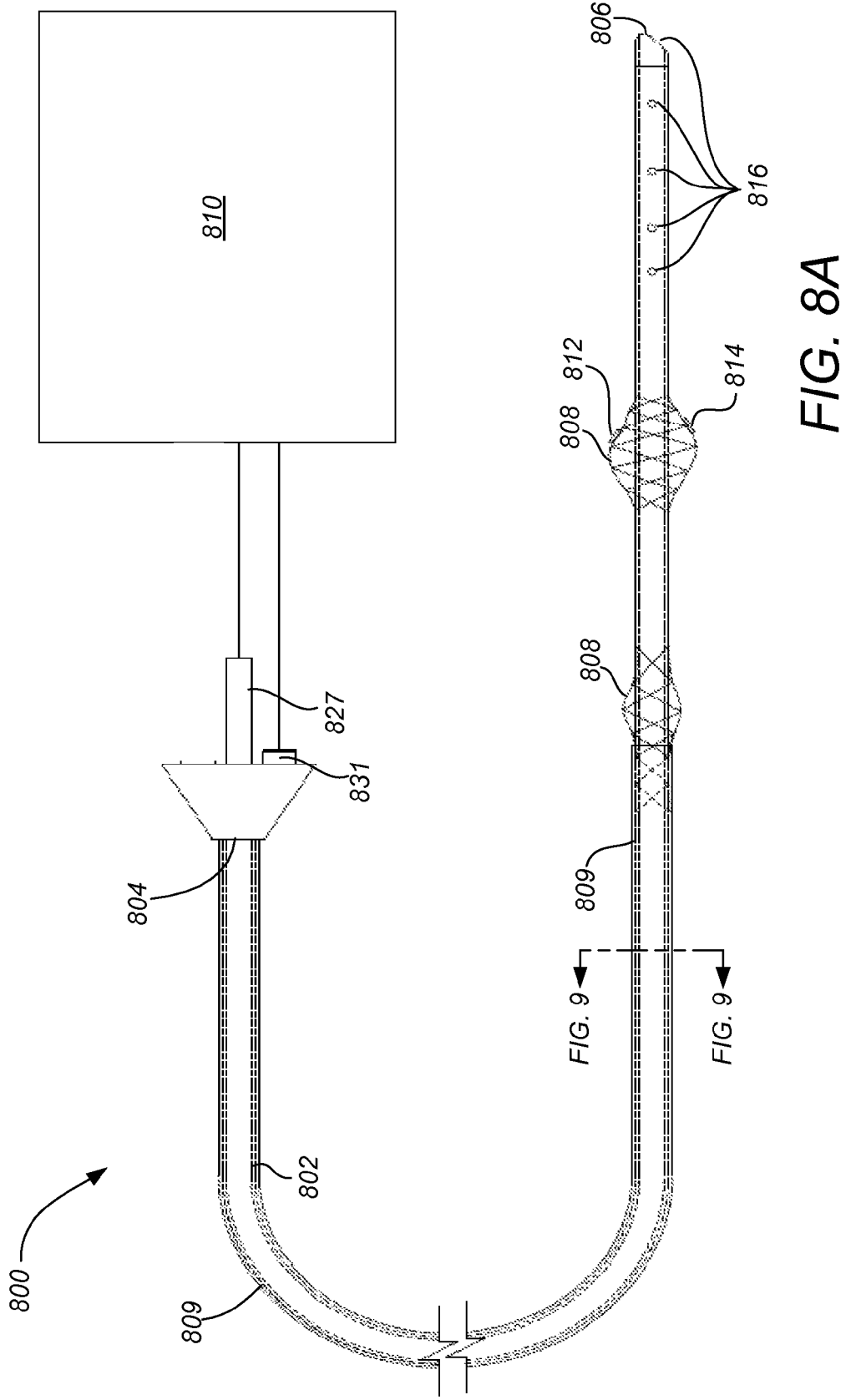

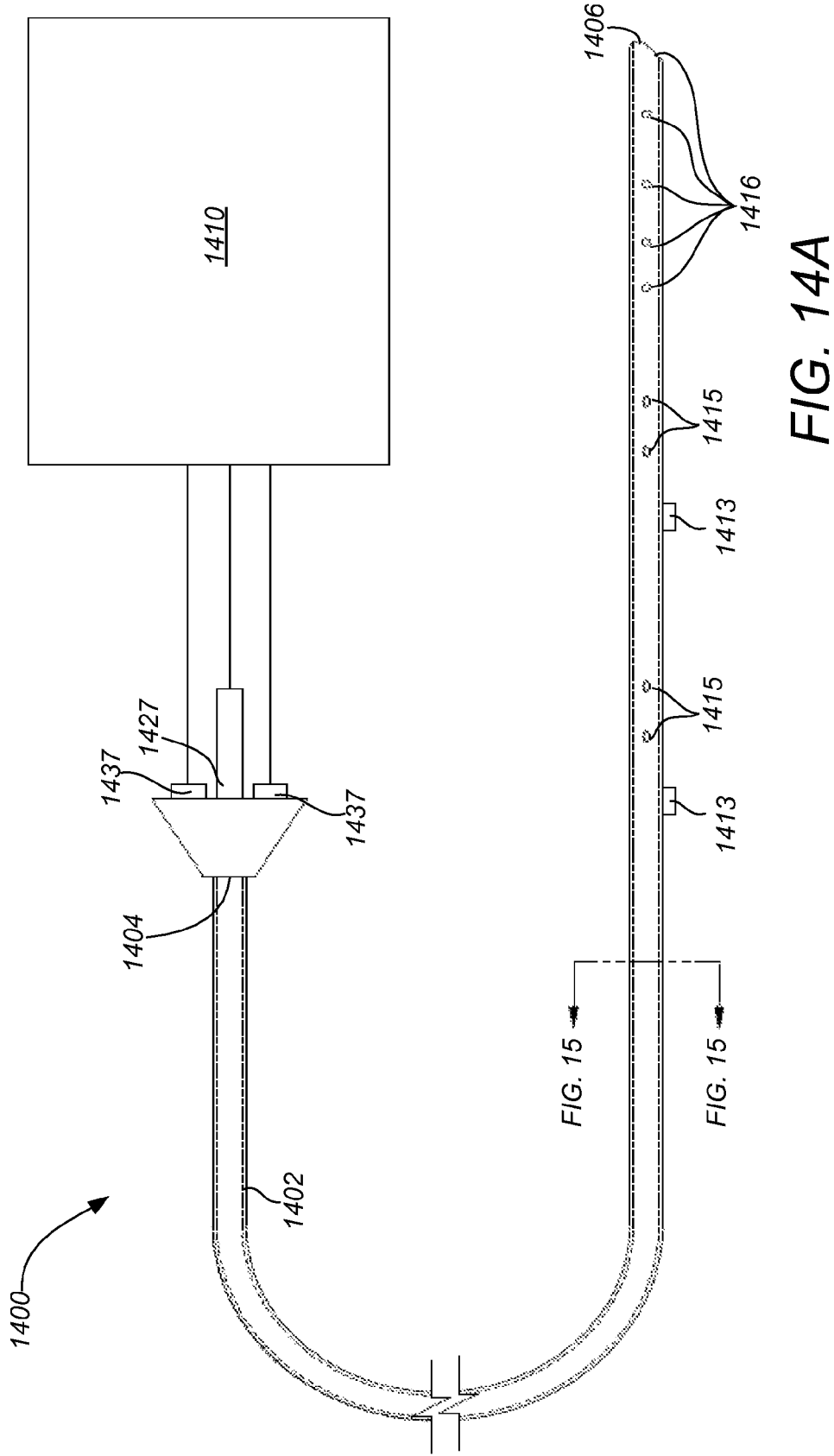

DEVICE FOR ELECTRICALLY AND MECHANICALLY STIMULATING A COMPARTMENT IN A BODY

BACKGROUND

Passage and propagation of food (solids and liquids) through the gastrointestinal (GI) tract is facilitated by the process of peristalsis. Peristalsis involves a distinct pattern of smooth muscle contractions of the gastrointestinal tract that facilitate the propulsion of food distally through the esophagus, stomach and intestines.

In addition to the natural pacing from the body, distension and mucosal irritation of the GI tract stimulates afferent neurons. These sensory neurons synapse with two sets of motor neurons, which lead to two distinct effects. In one instance, a group of sensory neurons activate excitatory motor neurons proximal to the bolus of food. The excitatory motor neurons stimulate contraction of smooth muscle. In another instance, a different group of sensory neurons activate inhibitory motor neurons. The inhibitory motor neurons relax smooth muscle distal to the bolus. The coordinated excitatory and inhibitory motor neuron activity propels the bolus of food forward. This process is repeated in a sequential pattern as it is regulated by the natural pacemaker frequency of the GI tract. Localized distension of the GI tract is a natural consequence of the process of peristalsis as the bolus of food is propelled forward.

Common motility disorders of the gastrointestinal tract are gastroparesis and ileus. Gastroparesis is a disorder that affects motility of the stomach in the absence of mechanical obstruction. Causes of gastroparesis are not fully understood but can be associated with diabetes, surgeries, medications, and disruption of normal neuronal stimulation of the GI tract. Surgical procedures, especially those involving the abdomen and thorax, can result in significant dysregulation of normal gastrointestinal activity. Disruption of normal peristalsis can lead to delayed gastric emptying and at the extreme, ileus. When ileus develops after a surgical procedure, it is commonly known as post-operative ileus (POI). POI is a major contributor to postoperative discomfort, prolonged hospitalization and surgical complications.

While a number of attempts have been made at electrically stimulating the GI tract, they have been ineffective in consistently stimulating peristaltic activity. These methods primarily use electrical stimulation applied via temporary or permanent leads/implants and can range from being highly invasive to being less invasive. In one example, electrical stimulation of the GI tract is applied immediately after a procedure via surgery and thus is not well tolerated by patients with pre-existing motility disorders and those already recovering from surgeries The discussion above is merely provided for general background information and is not intended to be used as an aid in determining the scope of the claimed subject matter.

SUMMARY

A device for stimulating select body tissues and organs from within a compartment in a body is provided. The device includes a multi-lumen tube positionable in the compartment of the body and having a proximal end and a distal end. At least one active portion is located along the tube between the proximal and distal ends and positioned proximate to select tissues and organs in the compartment of the body. The at least one active portion of the tube is configured to repeatedly provide mechanical distension and electrical stimulation to the select tissues and organs in the compartment of the body over a period of time.

At least one distendable element is coupled to the active portion of the tube. Each distendable element is configured to repeatedly expand against the select body tissues and organs within the compartment into a first position and contract within the compartment into a second position. At least one electrical component is coupled to the active portion of the tube. Each electrical component is in association with each of the distendable elements and configured to repeatedly activate and deactivate electrical stimulation to the select body tissues and organs.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

FIGS. 8A-8B are schematic diagrams of a device for stimulating select body tissues and organs from within a compartment under yet another embodiment.

FIG. 14A is schematic diagram of a device for stimulating select body tissues and organs from within a compartment under yet another embodiment.

DETAILED DESCRIPTION

Embodiments described herein relate to methods and devices for the treatment of disorders that pertain to gastric and intestinal motility. Disclosed methods and devices provide coordinated electrical, mechanical and hormonal stimulation in a gastrointestinal (GI) tract. However, disclosed methods and devices can provide electrical, mechanical and hormonal stimulation to any type of intraluminal or extraluminal compartment in the body.

Figure 1:
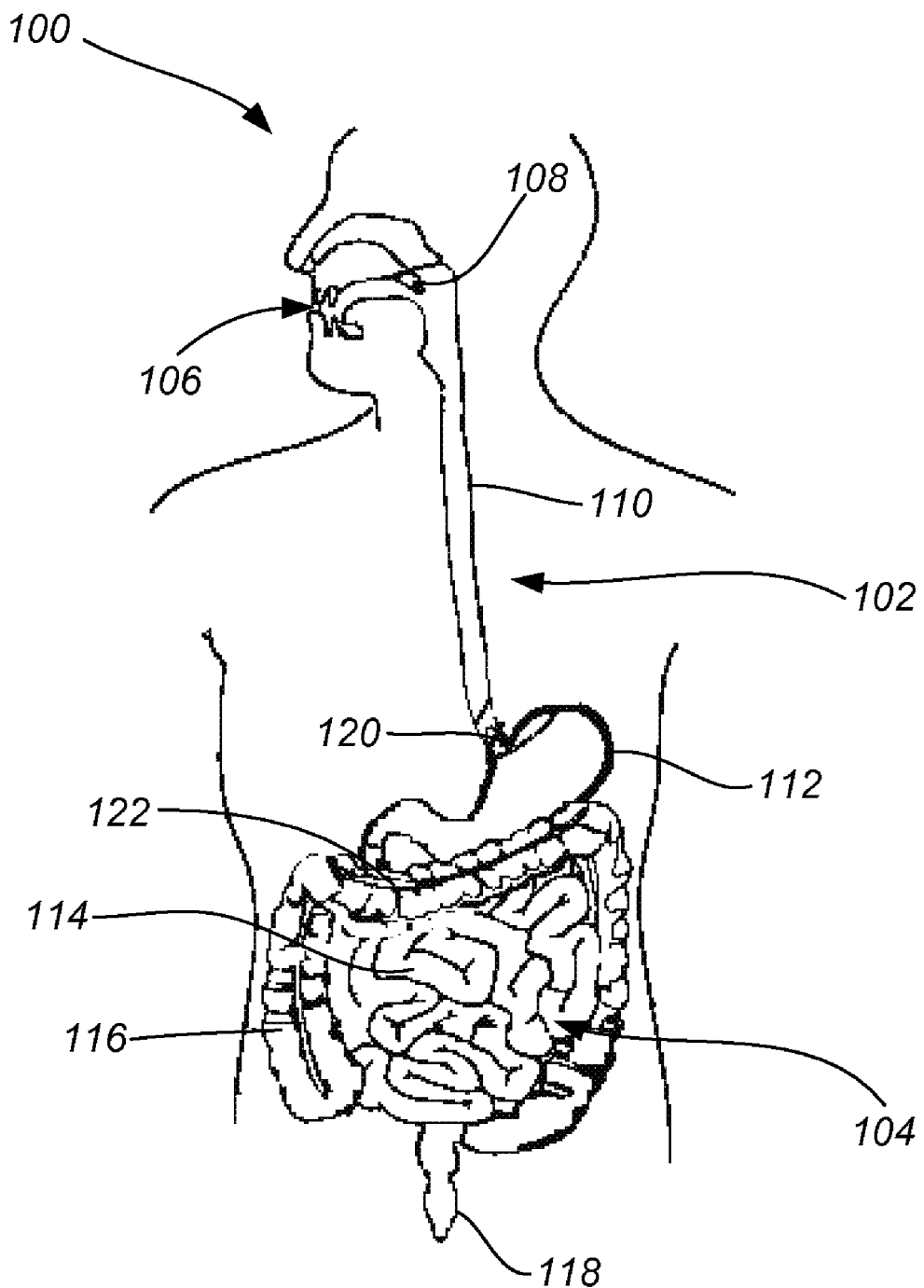
FIG. 1 is a diagrammatic view of a gastrointestinal (GI) tract.

A GI tract or digestive tract 100, as illustrated diagrammatically in FIG. 1, is a system of organs in a body that takes in food, digests the food to extract energy and nutrients and expels any remaining waste. GI tract 100 includes an upper GI tract 102 and a lower GI tract 104. The upper GI tract 102 includes a mouth 106, a pharynx 108, an esophagus 110 and a stomach 112. Normally, peristalsis (i.e., contraction of the muscles) in the esophagus 110 propels food from the mouth 106 and pharynx 108 to the stomach 112. The lower GI tract 104 includes small intestines 114, large intestines 116 and a rectum 118. The majority of digestion takes place in the small intestines 114. Food from the stomach is allowed into and pushed through the small intestines to the large intestines 116 by peristalsis. The large intestines 116 function as the last part of digestion and eliminate waste from the body via the rectum 118. The large intestines 116 also utilize peristalsis to push waste to the rectum 118.

Surgical procedures, especially those involving the abdomen and thorax, can result in significant dysregulation of normal gastrointestinal activity. Disruption of normal peristalsis can lead to delayed gastric emptying and at the extreme, ileus. Prolonged ileus can lead to malabsorption disorder, bowel ischemia, bowel perforation, and the need for invasive procedures such as exploratory laparotomy. Besides the negative effect on patient well-being, disruption of normal gastrointestinal motility is associated with increased length of hospital stay and surgical complications.

Embodiments described coordinate mechanical and electrical stimulation to the GI tract to increase the likelihood of facilitating normal GI activity, such as peristalsis. Embodiments described perform mechanical distension of the bowel at pressure ranges below that which will cause nociception, pain and inhibitory afferents. In particular, embodiments described perform mechanical distension at an intraluminal bowel pressure ranging from 6-10 mmHg to 20-40 mm Hg. Generally, embodiments described perform mechanical distension at an intraluminal bowel pressure that is less than 25 mmHg. Such a pressure is similar to the average capillary oncotic pressure, above which normal capillary blood flow can be inhibited due to compression of capillary walls. The repeat frequency can be as low as 1-2 cycles/minute and as high as 9-12 cycles/min.

Figure 2:
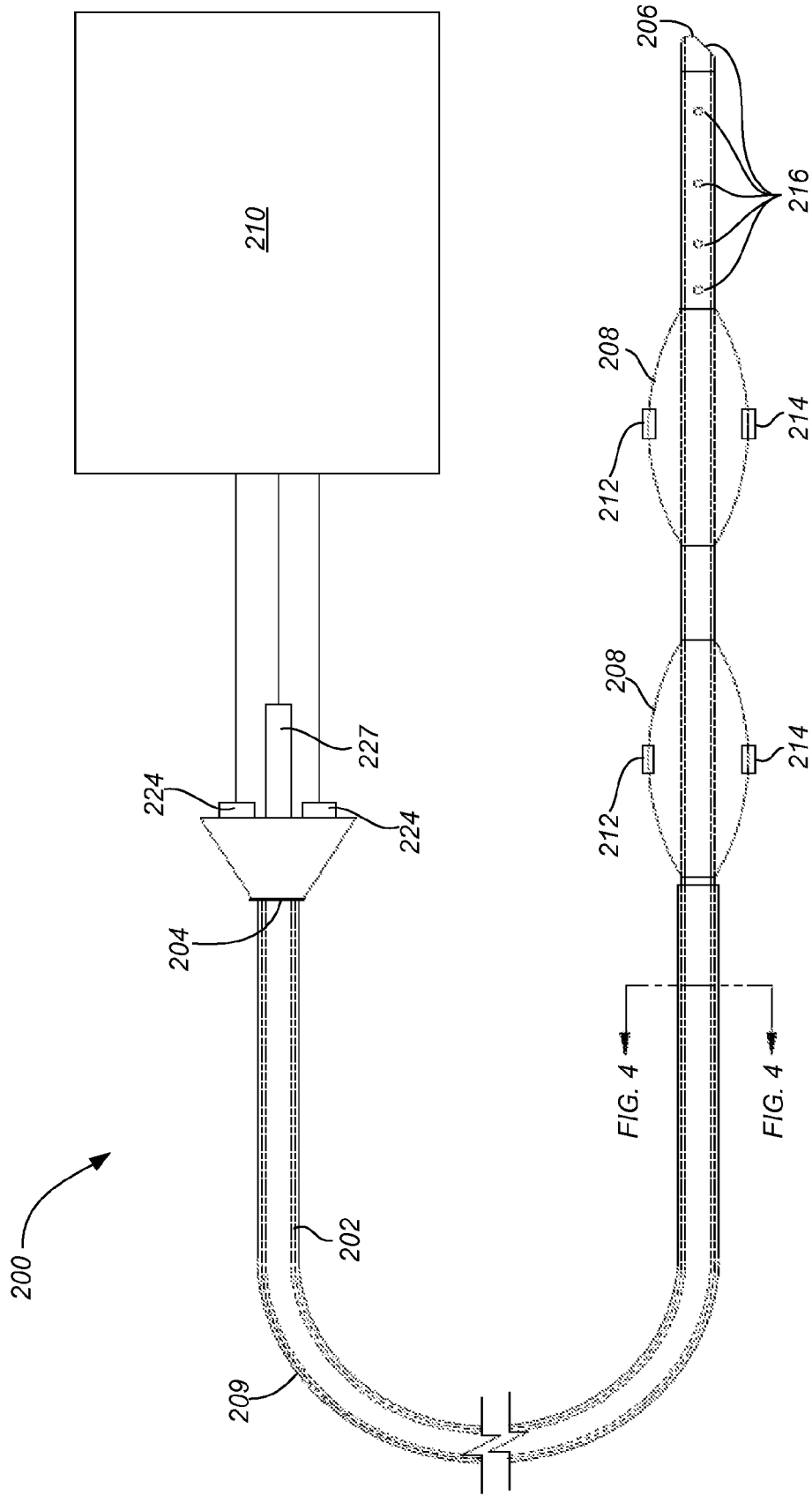
FIG. 2 is a schematic diagram of a device for stimulating select body tissues and organs from within a compartment under one embodiment.

FIG. 2 illustrates a device 200 for stimulating select body tissues and organs in a compartment under one embodiment. As discussed above, although device 200 will be discussed as being useful in a GI lumen, it should be understood that the device 200 can be useful in other lumens in a body.

Device 200 includes a tube or catheter 202 having a proximal end 204 and a distal end 206. Device 200 includes at least one distendable element 208 coupled to and located along tube 202. The at least one distendable element is in closer proximity to distal end 206 than proximal end 204. In the FIG. 2 embodiment, the distendable elements 208 are inflatable balloons. Inflatable balloons 208 are configured to repeatedly expand against the wall of a compartment, such as GI tract 100 (FIG. 1), into a first position and contract within a compartment into a second position. As illustrated in FIG. 2, both inflatable balloons 208 are in a first position or expanded position. Although device 200 includes two inflatable balloons 208, it should be realized that a single or any number of inflatable balloons 208 can be used.

Inflatable balloons 208 are in communication with a controller 210 via pneumatic connectors 224, which are coupled to proximal end 204 of tube 202. As illustrated in FIG. 2, inflatable balloons can be inflated synchronously and, although not specifically illustrated in FIG. 2, inflatable balloons can also be inflated asynchronously or in a time-related fashion from each other as determined by controller 210. Inflatable balloons 208 can be made of a number of different materials. For example, polyethylene, polyamides, polyvinyl chloride, polyvinyl alcohol, polypyrroles, polythiophenes and etc.

Device 200 also includes at least one electrical component in association with each of the distendable elements or inflatable balloons 208. The at least one electrical component is configured to repeatedly activate and deactivate electrical stimulation to the select body tissues and organs of the compartment in the same general vicinity as the expansion and contraction of the inflatable balloons 208. In one embodiment and as illustrated in FIG. 2, device 200 includes a cathode electrode 212 and an anode electrode 214 in contact with each inflatable balloon 208. As illustrated, electrodes 212 and 214 are located on the outer surface of each inflatable balloon 208. Cathode electrode 212 and anode electrode 214 provide electrical stimulation and are placed on opposite sides of each balloon 208. Electrodes 212 and 214 can also be configured to sense the natural electrical activity or myoelectrical activity of the compartment within which device 200 is located.

Electrodes 212 and 214 are in communication with controller 210 via electrical leads that run from electrodes 212 and 214 to a multi-pin electrical connector 227, which is coupled to proximal end 204 of tube. Electrical leads are illustrated and described in more detail in the sectional view of tube 202 in FIG. 4.

In another embodiment, one of an anode or a cathode electrode can be in contact with the outer surface of each inflatable balloon 208. The anode or cathode electrode on each inflatable balloon 208 can then share a common electrode of opposite polarity that can be located on tube 202 or on one of the inflatable balloons. For example, a positive electrode can be located on each balloon 208 and a common, shared negative electrode can be located on tube 202. Although electrodes 212 and 214 can both be located on balloons 208 as illustrated, it should be realized that electrodes 212 and 214 can be located on the tube 202 or located on both the balloons 208 and the tube 202.

As also illustrated in FIG. 2, device 200 includes a plurality of outlets 216 located proximate distal end 206 along the sides of the tube proximate distal end 206 as well as at distal end 206. In an alternative embodiment, an outlet can be located just at distal end 206 or outlets can be just located along the side proximate distal end 206. Outlets 216 are for the evacuation and delivery of fluids and solids into the compartment. For example, outlets 216 can be used for evacuating GI tract contents or for the delivery or administration of medicines, food or hormonal stimulants. The delivery of fluids and solids is similar to a nasogastric tube for use in a GI tract. Although not particularly illustrated in FIG. 2, additional or alternative outlets other than the outlets 216 shown in FIG. 2 can be included in device 200. For example, outlets can be located proximal, in between and/or distal to the distendable elements 208. Locations of outlets can vary depending on the intended anatomical location of tube 202 and the portion or portions of the compartment or GI tract that requires evacuation. A discussion in regards to different anatomical placements for tube 202 will be discussed in detail in FIGS. 17 and 18.

In one embodiment, tube 202 can optionally include a sheath 209. During insertion, sheath 209 can cover the entire outer surface of tube 202 including balloons 208 and the portion of tube 202 that includes outlets 216 to protect the balloons and electrodes or to protect the GI tract from device 200. After insertion, sheath 209 is retracted to expose balloons 208 and electrodes 212 and 214 for stimulating the GI tract.

Figure 3:
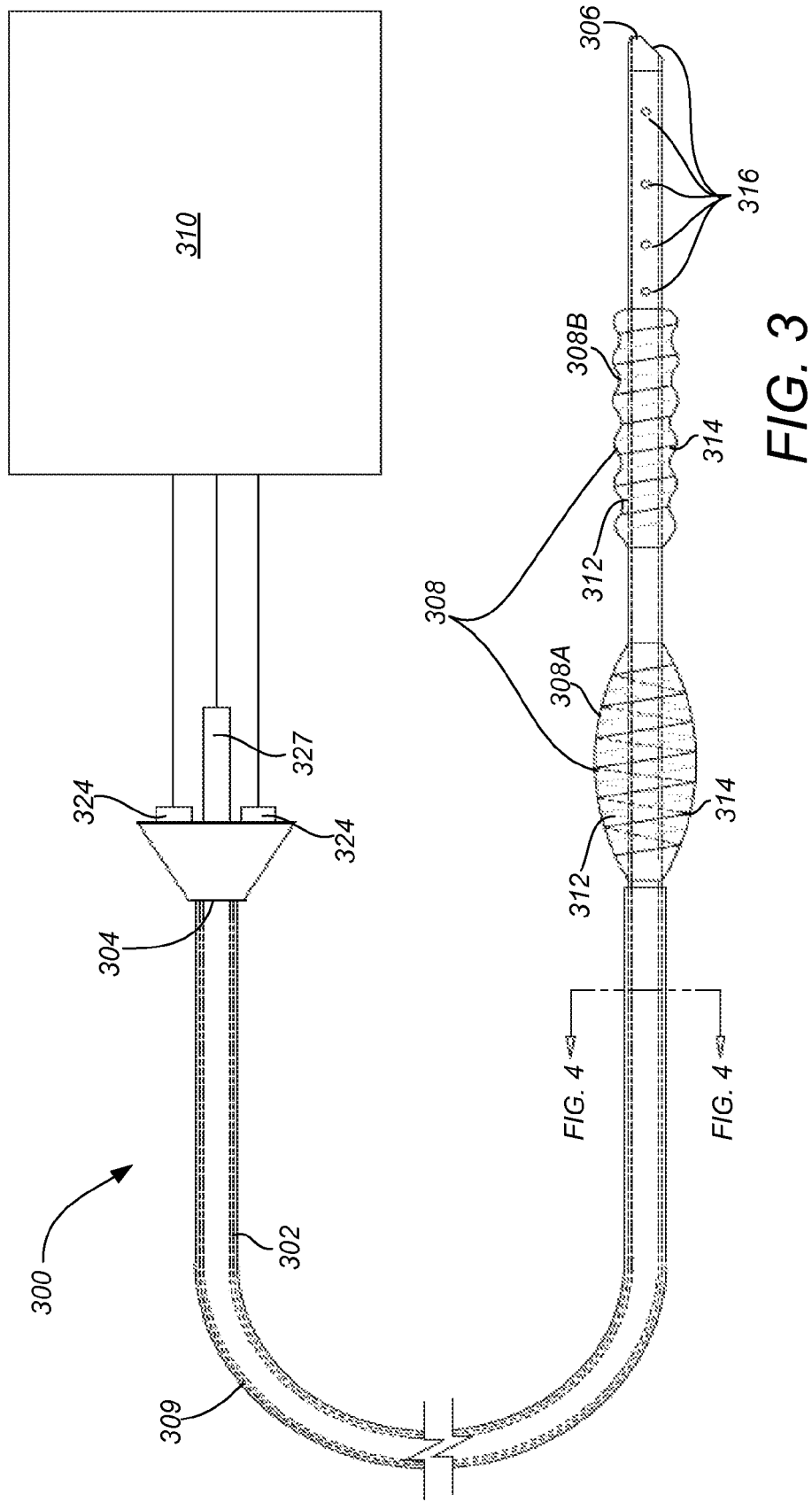
FIG. 3 is a schematic diagram of a device for stimulating select body tissues and organs from within a compartment under another embodiment.

FIG. 3 illustrates a device 300 for stimulating select body tissues and organs in a compartment under another embodiment. As discussed above, although device 300 will be discussed as being useful in a GI lumen, it should be understood that the device 300 can be useful in other lumens in a body.

Device 300 is similar to device 200 in that it includes a tube or catheter 302 having a proximal end 304 and a distal end 306 and at least one distendable element 308 coupled to and located along tube 302. The at least one distendable element is in closer proximity to distal end 306 than proximal end 304. Like device 200, the pair of distendable elements 308 are inflatable balloons configured to repeatedly expand against a compartment, such as a GI tract, into a first position and contract within the compartment into a second position. As illustrated in FIG. 3, inflatable balloon 308A is in a first position or expanded position and inflatable balloon 308B is in a second position or contracted position. Although device 300 includes two inflatable balloons 308, it should be realized that a single or any number of inflatable balloons 308 can be used.

Inflatable balloons 308A and 308B are in communication with a controller 310 via pneumatic connectors 324, which are coupled to proximal end 304 of tube 302. Like device 200, inflatable balloons 308 can be inflated asynchronously or in a time-related fashion from each other and, although not specifically illustrated in FIG. 3, inflatable balloons can also be inflated synchronously as determined by controller 310. The inflatable balloons 308 can be made of similar materials to the inflatable balloons 208 of FIG. 2.

Device 300 includes a different type of electrical stimulation than that of device 200. The at least one electrical component of device 300 is configured to repeatedly activate and deactivate electrical stimulation to the select body tissues and organs of a compartment in the same general vicinity as the expansion and contraction of inflatable balloons 308 like device 200. However, in the FIG. 3 embodiment, each balloon 308 is surrounded by and in contact with a coiled ring or ribboned cathode electrode 312 and a coiled ring or ribboned anode electrode 314. Electrodes 312 and 314 are in contact with the outer surface of each inflatable balloon 308. Coiled electrode 312 and coiled electrode 314 provide repeated electrical stimulation and are configured to allow expansion of the balloon so that both mechanical distension as well as electrical contact with the compartment wall is achieved.

Electrodes 312 and 314 can be made of an inextensible metal that can be arrayed over a balloon or other expandable member without preventing it from expanding. For example, wire can be wound back and forth across the faces of a balloon such that the end wraps are close to the tube where the balloon expands the least, and the straight runs of wire are situated to allow expansion. In another embodiment, coiled electrodes 312 and 314 can be a printed conductive ink placed on the balloon to achieve the same effect as the metal wire or ribbon embodiment. As discussed above, electrodes 312 and 314 are disposed on the outer surface of the expanding portion of the balloons to ensure optimal physical contact between the electrodes and the wall of the compartment. It also keeps the point of application of the mechanical stimulation (balloon expansion) and electrical stimuli (electrodes) in close physical proximity which could maximize synergistic effects.

Electrodes 312 and 314 are in communication with controller 310 via electrical leads that run from electrodes 312 and 314 to a multi-pin electrical connector 327, which is coupled to proximal end 304 of tube 302. Electrical leads are illustrated and described in more detail in the sectional view of tube 303 in FIG. 4.

Although electrodes 312 and 314 can both surround balloons 308, it should be realized that electrodes 312 and 314 can surround the tube 302 or surround both the balloons 308 and the tube 302. For example, a positive electrode can surround each balloon 308 and a common, shared negative electrode can surround tube 302.

Like device 200, device 300 also includes a plurality of outlets 316 located along the sides of the tube 302 proximate distal end 306 as well as at distal end 306 for the evacuation and delivery of fluids and solids into the compartment. In particular, outlets 316 can deliver a hormonal stimulant. In an alternative embodiment, a single outlet can be located at distal end 306 or outlets can be located along the side proximate distal end 306. Although not particularly illustrated in FIG. 3, additional or alternative outlets other than the outlets 316 shown in FIG. 3 can be included in device 300. For example, outlets can be located proximal, in between and/or distal to the distendable elements 308. Locations of outlets can vary depending on the intended anatomical location of tube 302 and the portion or portions of the compartment or GI tract that requires evacuation as will be discussed in detail in FIGS. 17 and 18.

In one embodiment, tube 302, like tube 202, can optionally include a sheath 309. During insertion, sheath 309 can cover the entire outer surface of tube 302 including balloons 308 and the portion of tube 302 that includes outlets 316 to protect the balloons and electrodes or to protect the GI tract form device 300. After insertion, sheath 309 is retracted to expose balloons 308 and electrodes 312 and 314 for stimulating the GI tract.

Figure 4:
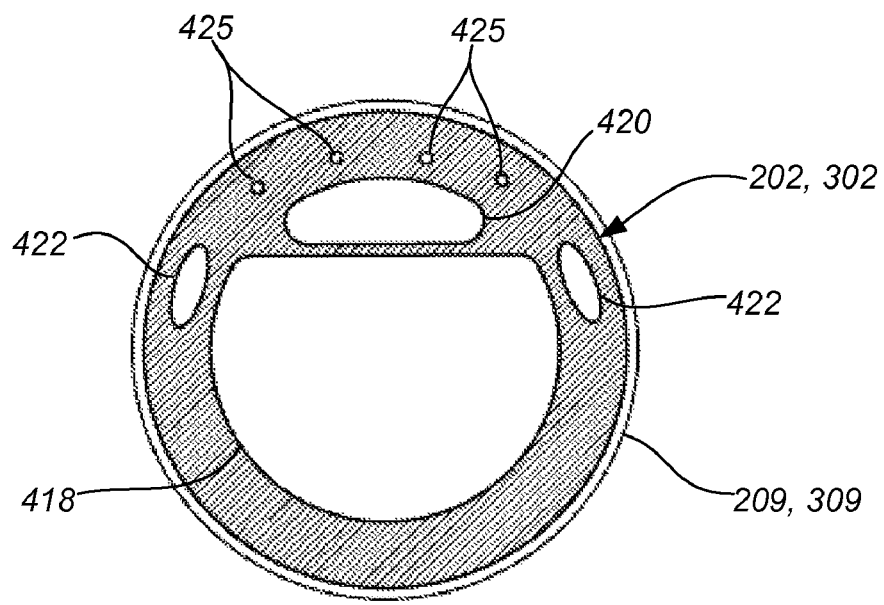
FIG. 4 is a sectional view of a tube of the devices illustrated in FIGS. 2 and 3.

FIG. 4 illustrates a sectional view of tubes 202 and 302. As illustrated, tubes 202, 302 are multi-lumen flexible tubes surrounded by a sheath 209, 309. At least one lumen or primary lumen 418 of tubes 202, 302 is of a sufficient diameter to function for the evacuation and delivery of fluids and solids, such as a hormonal stimulant. A secondary lumen 420 acts as a vent or flush port. Primary lumen 418 and secondary lumen 420 extend from at least one of the outlets 216 of device 200 and at least one of the outlets 316 of device 300 to connectors at proximal end 204, 304 (not illustrated in FIG. 2 or 3). In one embodiment, primary lumen 418 can be coupled to controller 210, 310. However, in other embodiments, primary lumen 418, like secondary lumen 420, need not be controlled by controller 210, 310.

Tube 202, 302 also includes tertiary lumens 422. Each tertiary lumen 422 extends from each balloon 208, 308 to pneumatic connectors 224, 324 at proximal end 204, 304 and are used for the inflation and deflation of each balloon coupled to tube 202, 302. As discussed above, each pneumatic connector 224, 324 are coupled to controller 210, 310. Tubes 202, 302 also include electrical leads 425 that provide electrical energy to each electrode of devices 200 and 300. In FIG. 4, tubes 202, 302 includes two tertiary lumens 422, one for each of the pair of balloons 208 and 308, while tubes 202, 302 include four electrical leads 425, one for each of the two cathode electrodes 212 and 312 and one for each of the two anode electrodes 214 and 314 of devices 200 and 300. However, it should be realized that tubes 202, 302 can include any number of electrical leads 425 depending on the amount of electrodes. For example, tubes 202, 302 can include three electrical leads 425 in the case where two of the leads are for positive electrodes and one of the leads is for a shared negative electrode. Tertiary lumens 422 and electrical leads 425 travel from their connections to balloons 208, 308 or electrodes 212, 312 and 214, 314 to electrical connector 227, 327 located at proximal end 204, 304 that is coupled to controller 210, 310.

Electrodes 212 and 214 illustrated in FIG. 2 and coil ringed or ribboned electrodes 312 and 314 illustrated in FIG. 3 can have simple exposed conductors or they can have additional electrically conductive material added to the conductor to increase the exposed surface area. For example, conductive gels, conductive inks or epoxies or solid metallic "spreaders" can be placed at the end of an electrode lead 225 or 325 to improve surface contact between the electrode and the wall of the compartment. Additional electrically conductive material can be located on the distendable elements, along the tube or both. In the case where a positive electrode is located on each balloon and a negative electrode is located on the tube is an example configuration for placing electrically conductive material on both the distendable elements and the tube.

Figure 5:
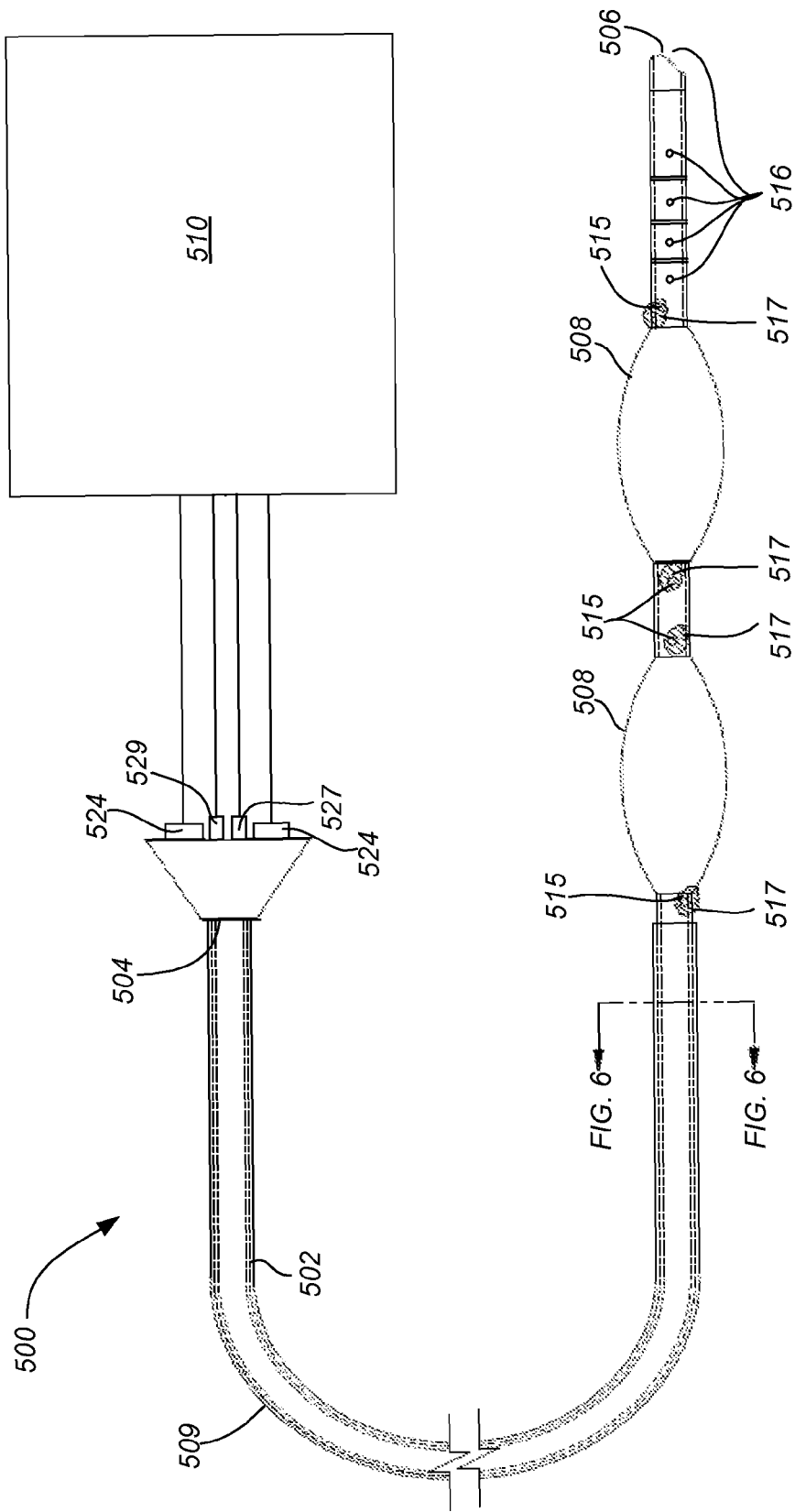
FIG. 5 is schematic diagram of a device for stimulating select body tissues and organs from within a compartment under yet another embodiment.

FIG. 5 illustrates a device 500 for stimulating select body tissues and organs in a compartment under another embodiment. As discussed above, although device 500 will be discussed as being useful in a GI lumen, it should be understood that the device 500 can be useful in other lumens in a body.

Device 500 is similar to devices 200 and 300 in that it includes a tube or catheter 502 having a proximal end 504 and a distal end 506 and at least one distendable element 508 coupled to and located along tube 502. The at least one distendable element 508 is in closer proximity to distal end 506 than proximal end 504. Like devices 200 and 300, the pair of distendable elements 508 are inflatable balloons configured to repeatedly expand against a compartment, such as a GI tract, into a first position and contract within the compartment into a second position. As illustrated in FIG. 5, inflatable balloons 508 are in a first position or expanded position. Although device 500 includes two inflatable balloons 508, it should be realized that a single or any number of inflatable balloons 508 can be used.

Inflatable balloons 508 are in communication with a controller 510 via pneumatic connectors 524, which are coupled to proximal end 504 of tube 502. Like devices 200 and 300, inflatable balloons 508 can be inflated synchronously and, although not specifically illustrated in FIG. 5, inflatable balloons can also be inflated asynchronously or in a time-related fashion from each other as determined by controller 510. The inflatable balloons 508 illustrated in FIG. 5 can be made of similar materials to the inflatable balloons 208 of FIG. 2 and inflatable balloons 308 of FIG. 3.

Device 500 includes a different type of electrical stimulation then that of devices 200 and 300. The at least one electrical component of device 500 is configured to repeatedly activate and deactivate electrical stimulation to the select body tissues and organs of the compartment like devices 200 and 300. However, in the FIG. 5 embodiment, device 500 includes a plurality of pores 515. Pores 515 are in communication with controller via a connector 529, which is coupled to proximal end 504 of tube 502.

Pores 515 are configured to dispense conducting gel 517 that acts as electrodes. Conducting gel 517 can achieve good apposition against a wall of a compartment. Examples of suitable materials for use in making a conductive gel electrode could include, but are not limited to, electrically conductive hydrogels similar to those found on ECG leads, silicone gel doped with a carbon or electrically conductive filler, or any conformable material capable of conducting electricity. Just as coiled rings or ribbon electrodes illustrated in FIG. 3 increase the surface area of the electrode in contact with a wall of a compartment without compromising the ability of the balloons to inflate and provide mechanical distension; a gel electrode dispensed into the compartment allows for increased contact area and can also act to inflate the balloons. While in FIG. 5, pores 515 are located on tube 502, it is possible for pores to be located in balloons 508 or on tube 502 and balloons 508. If pores 515 are located in balloons 508, it is possible for connector 529 and connectors 524 to be in one single connection. In this embodiment, besides conducting gel 517 acting as an electrode, conducting gel 517 can also inflate balloons 508.

To assist conducting gel 517 in electrical stimulation, pores 515 can also be in communication with controller 510 via electrical leads that run from pores 515 to an electrical connector 527 located at proximal end 504 of device 500. Electrical leads are illustrated and described in more detail in the sectional view of tube 502 in FIG. 6.

Like devices 200 and 300, device 500 also includes a plurality of outlets 516 located along the sides of the tube proximate distal end 506 as well as at distal end 506 for the evacuation and delivery of fluids and solids, such as a hormonal stimulant, into the compartment. In an alternative embodiment, a single outlet can be located at distal end 506 or outlets can be located just along the side proximate distal end 506. Although not particularly illustrated in FIG. 5, additional or alternative outlets other than the outlets 516 shown in FIG. 5 can be included in device 500. For example, outlets can be located proximal, in between and/or distal to the distendable elements 508. Locations of outlets can vary depending on the intended anatomical location of tube 502 and the portion or portions of the compartment or GI tract that requires evacuation as will be discussed in detail in FIGS. 17 and 18.

In one embodiment, tube 502, like tubes 202 and 302, can optionally include a sheath 509. During insertion, sheath 509 can cover the entire outer surface of tube 502 including balloons 508 and the portion of tube 502 that includes outlets 516 to protect the balloons and electrodes or to protect the GI tract from device 500. After insertion, sheath 509 is retracted to expose balloons 508 and pores 515 for stimulating the GI tract.

Figure 6:
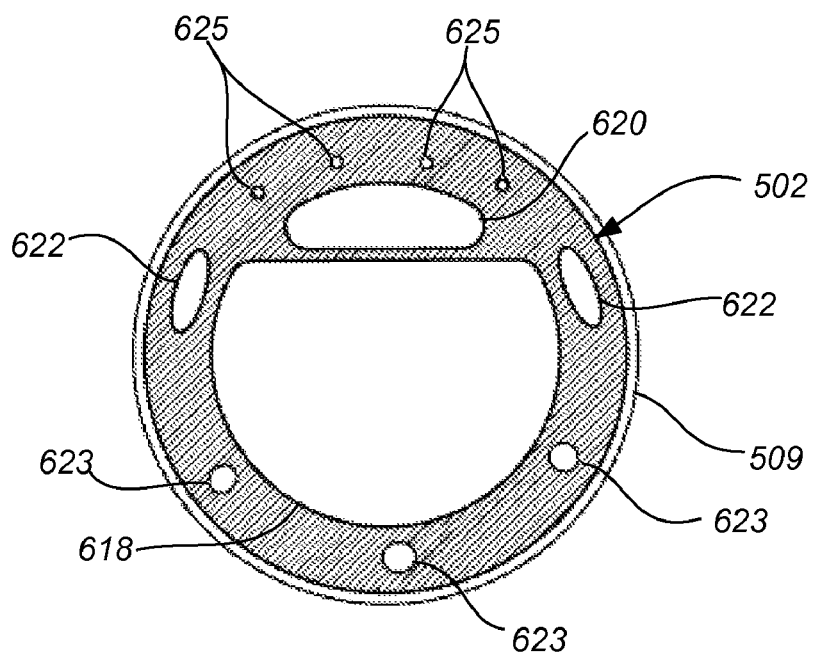
FIG. 6 is a sectional view of a tube of the device illustrated in FIG. 5.

FIG. 6 illustrates a sectional view of tube 502 of device 500. As illustrated, tube 502 is a multi-lumen flexible tube surrounded by a sheath 509. At least one lumen or primary lumen 618 of tube 502 is of a sufficient diameter to function for the evacuation and delivery of fluids and solids, such as a hormonal stimulant. A secondary lumen 620 acts as a vent or flush port. Primary lumen 618 and secondary lumen 620 extend from at least one of the outlets 516 of device 500 to connect to connectors at proximal end 504 (not illustrated in FIG. 5). In one embodiment, primary lumen 618 can be coupled to controller 510. However, in other embodiments, primary lumen 618, like secondary lumen 620, need not be controlled by controller 510.

Tube 502 also includes tertiary lumens 622 for the inflation and deflation of each balloon coupled to tube 502. Quaternary lumens 623 are also provided in tube 502 for providing conducting gel to pores 515 for activating and deactivating electrical stimulation of the compartment. Electrical leads 625 provide electrical energy to the conducting gel 517 and pores 515. In FIG. 5, tube 502 includes two tertiary lumens 622, one for each of the pair of balloons 508, while tube 502 includes four electrical leads 624, one for each of pores 515. In FIG. 5, tube 502 includes three conducting gel paths 623; one for each positive gel electrode and a common path for the negative gel electrode.

Figure 7:
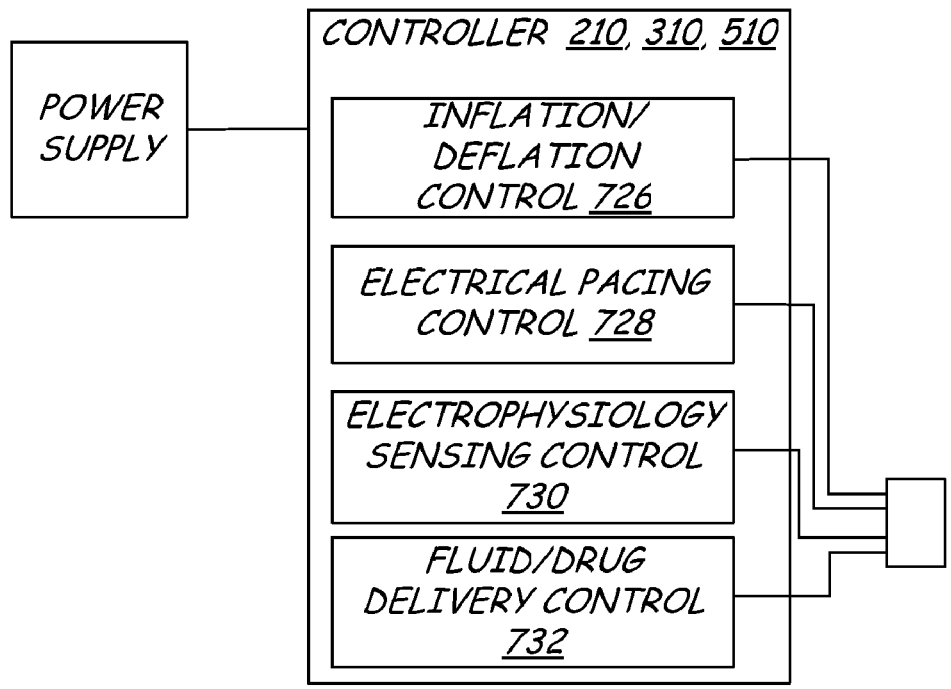
FIG. 7 is a block diagram of a controller of the devices illustrated in FIGS. 2, 3 and 5.

FIG. 7 illustrates a block diagram of controllers 210, 310 and 510 illustrated in FIGS. 2, 3 and 5. Controllers 210, 310 and 510 include an inflation/deflation control 726, an electrical pacing control 728, an electrophysiological sensing control 730 and an optional fluid/drug delivery/suction control 732. Controller is powered by a power supply as illustrated. Inflation/deflation control 726 operates to provide a fluid through tertiary lumens 422 (FIG. 4) and 622 (FIG. 6) for controlled expansion to balloons in devices 200, 300 and 500 and controlled contraction to the balloons. For example, in the embodiments illustrated in FIGS. 2, 3 and 5, air or other type of gas or liquid can be used to inflate each balloon. In the FIG. 5 embodiment, however, another option is to use conducting gel to inflate each balloon. Of course, it is recognized that the expansion and contraction of balloons can be manually performed without the use of controller 210, 310 and 510 as well. Electrical pacing control 728 operates to provide electrical energy through electrical leads 425, 625 for controlled activation and deactivation of electrodes when electrical pacing control 728 is controlling devices 200, 300 and 500. In another embodiment, electrical pacing control 728 operates to provide and evacuate electrical conducting gel through lumens 622 in FIG. 5 in combination with electrical leads 625 for the activation and deactivation of electrical energy.

Electrophysiological sensing control 730 operates to gather data related to sensing of a compartment in the body when electrodes also function to sense activity in the compartment. For example, when the compartment is a GI tract, electrodes can sense gastrointestinal activity or myoelectrical activity. Fluid/drug delivery/suction control 732 provides and evacuates fluids and solids, such as hormonal stimulant, to and from the compartment through primary lumen 418 and 618. Again, control 732 could be eliminated and fluid/drug delivery/suction can occur with some other means. Through primary lumen 418 and 618, control 732 can feed and administer drugs and other oral agents by either supplying minimal amounts of oral fluids or supplying a continuous stream of oral fluids. Through primary lumen 418 and 618, control 732 can also aspirate or drain the contents in the compartment, such as aspirate or drain gastric secretions or swallowed air.

Figure 8B:
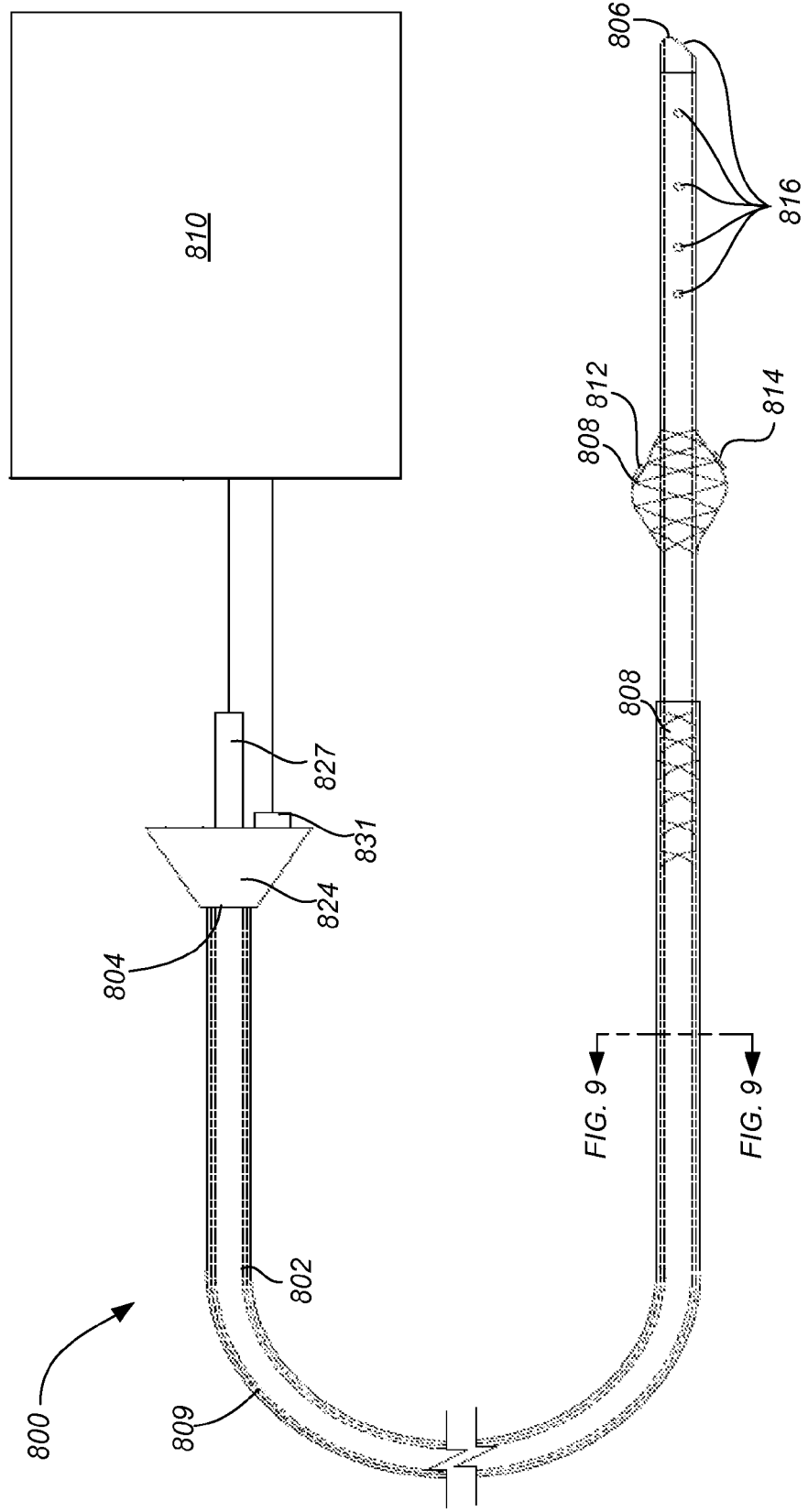

FIGS. 8A and 8B illustrate a device 800 for stimulating select body tissues and organs in a compartment under yet another embodiment. As discussed above, although device 800 will be discussed as being useful in a GI lumen, it should be understood that the device 800 can be useful in other lumens in a body.

Device 800 is similar to devices 200, 300 and 500 in that it includes a tube or catheter 802 having a proximal end 804 and a distal end 806 and at least one distendable element 808 coupled to and located along tube 802. The at least one distendable element is in closer proximity to distal end 806 than proximal end 804. Unlike devices 200, 300 and 500, device 800 includes distendable elements 808 that are reversibly deformable under a constraining component, such as a sheath 809. In other words, each distendable element 808 is self-expanding into an expanded state and constrained by a retractable sheath 809 into a compressed state.

As illustrated in FIG. 8A, a single sheath 809 is configured to surround the elements 808 when device 800 is to be inserted into a compartment. To allow the element to repeatedly expand against a compartment into a first position and contract within the compartment into a second position, sheath 809 is slid away from elements 808 such that they self-expand into the first position and sheath 809 is slid over the elements 808 to constrain them into the second position. In FIG. 8A, one of the elements 808 is being constrained into a contraction, while in FIG. 8B, one of the elements 808 is fully constrained into the contraction. Sheath 809 can be in communication with a controller 810 via a connector 831, which is coupled to proximal end 804 of tube 802. However, it should be realized that device 800 can include a pair of sheaths 809 for each element 808 and, therefore, device 800 could have a connector 831 for each sheath 809. Although device 800 includes two elements 808, it should be realized that a single or any number of elements 808 can be used.

Device 800 also includes at least one electrical component in association with each of the distendable elements 808. The at least one electrical component is configured to repeatedly activate and deactivate electrical stimulation to the select body tissues and organs of the compartment in the same general vicinity as the expansion and contraction of elements 808. In the FIG. 8 embodiment, each element 808 (although in FIGS. 8A and 8B only one of the elements illustrates electrodes) of device 800 can include a cathode electrode 812 and an anode electrode 814 similar to and described in regards to device 200 of FIG. 2. However, the FIG. 8 embodiment can include other types of electrical components, such as the coiled ringed or ribboned electrodes illustrated and discussed in FIG. 3 or the use of conducting gel as an electrode as discussed and illustrated in FIG. 5, but without the use of conducting gel to expand the elements 808. Electrodes 812 and 814 can also be configured to sense the natural electrical activity of the compartment within which device 800 is located.

Electrodes 812 and 814 are in communication with controller 810 via electrical leads that run from electrodes 812 and 814 to a multi-pin electrical connector 827, which is coupled to proximal end 804 of tube 802. Electrical leads are illustrated and described in more detail in the sectional view of tube 802 in FIG. 9.

Like devices 200, 300 and 500, device 800 includes a plurality of outlets 816 located along the sides of the tube 802 proximate distal end 806 as well as at distal end 806 for the evacuation and delivery of fluids and solids, such as a hormonal stimulant, into the compartment. In an alternative embodiment, an outlet can be located just at distal end 806 or outlets can be located just along the side proximate distal end 806. Although not particularly illustrated in FIG. 8, additional or alternative outlets other than the outlets 816 shown in FIG. 8 can be included in device 800. For example, outlets can be located proximal, in between and/or distal to the distendable elements 808. Locations of outlets can vary depending on the intended anatomical location of tube 802 and the portion or portions of the compartment or GI tract that requires evacuation as will be discussed in detail in FIGS. 17 and 18.

Figure 9:
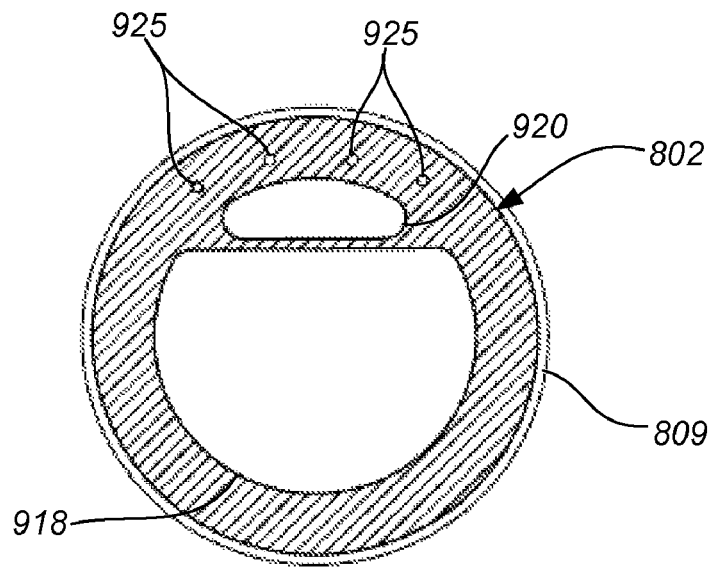
FIG. 9 is a sectional view of a tube of the device illustrated in FIGS. 8A and 8B.

FIG. 9 illustrates a sectional view of tube 802 of device 800. As illustrated, tube 802 is a multi-lumen flexible tube and includes removable sheath 809 that surrounds tube 802. However, in other embodiments not illustrated, tube 802 can include a sheath for each distendable element. In such an embodiment, tube 802 can include an additional lumen to provide control to a distal sheath independently of a proximal sheath. As discussed above, sheath 809 allows distendable elements to self-expand. At least one lumen or primary lumen 918 of tube 802 is of a sufficient diameter to function for the evacuation and delivery of fluids and solids, such as a hormonal stimulant. A secondary lumen 920 acts as a vent or flush port. Primary lumen 918 and secondary lumen 920 extend from at least one of the outlets 816 of device 800 to connect to connectors at proximal end 804 (not illustrated in FIG. 8A or 8B). In one embodiment, primary lumen 918 can be coupled to controller 810. However, in other embodiments, primary lumen 918, like secondary lumen 920 need not be controlled by controller 810.

Tube 802 also includes electrical leads 925 that provide electrical energy to electrodes 812 and 814 that are in association with the distendable elements. In FIG. 9, tube 802 includes four electrical leads 924, one for each of two cathode-type electrodes 812 and one for each of two anode-type electrodes 814. Electrical leads 925 travel from their connections to distendable elements 808 to an external connector 827 that is coupled to controller 810. However, it should be realized that tube 802 can include any number of electrical leads 925.

Figure 10:
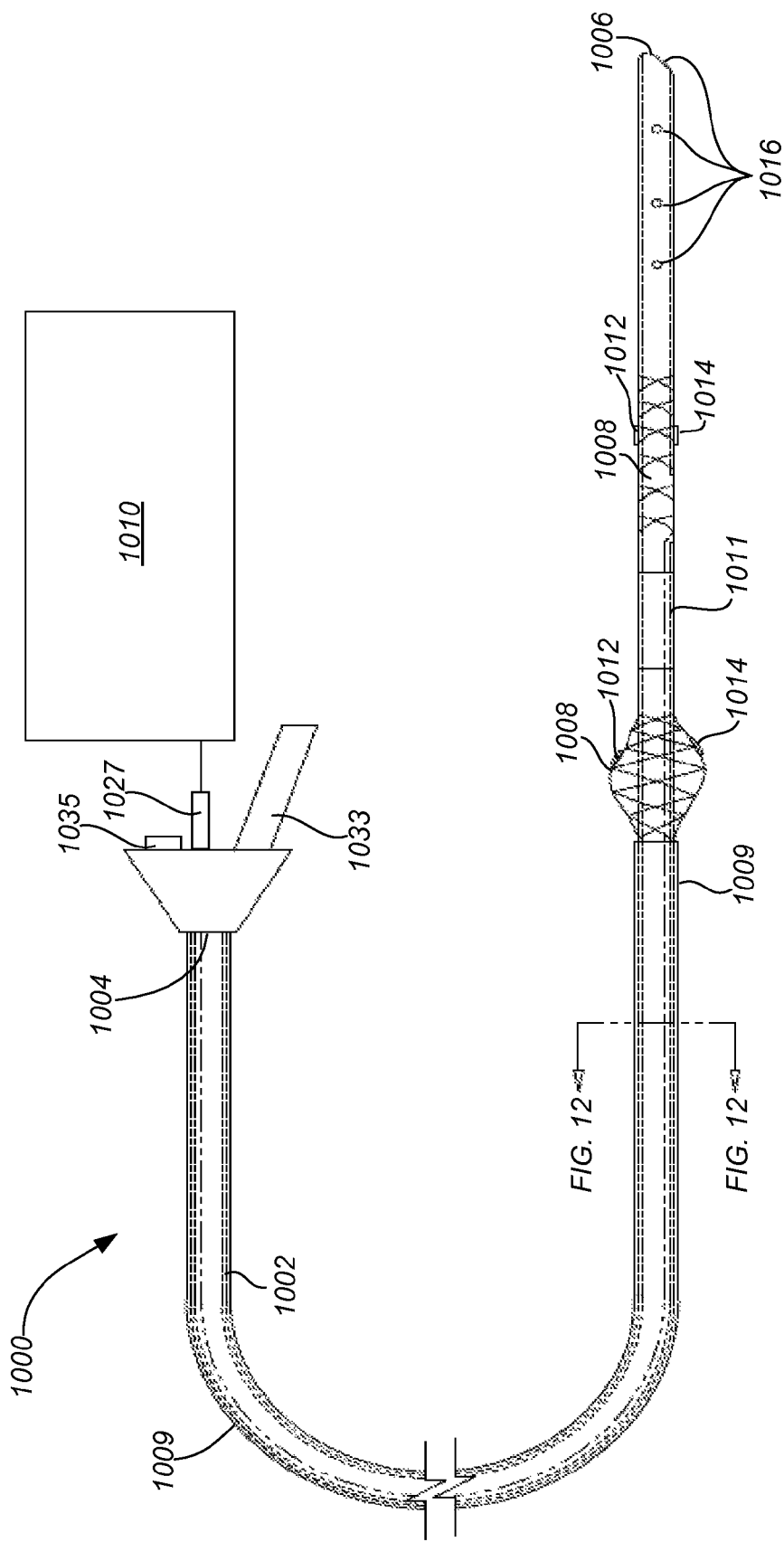
FIG. 10 is schematic diagram of a device for stimulating select body tissues and organs from within a compartment under yet another embodiment.

FIG. 10 illustrates a device 1000 for stimulating select body tissues and organs in a compartment under yet another embodiment. As discussed above, although device 1000 will be discussed as being useful in a GI lumen, it should be understood that the device 1000 can be useful in other lumens in a body.

Device 1000 is similar to device 800 in that it includes a tube or catheter 1002 having a proximal end 1004 and a distal end 1006 and at least one distendable element 1008 coupled to and located along tube 1002. The at least one distendable element is in closer proximity to distal end 1006 than proximal end 1004. Unlike device 800, the distendable elements disposed along tube 1002 are mesh cylinders 1008, which can be metallic or a polymer, that radially expand into a first position and contract into a second position using a mandrel 1011 that is attached to the ends of a mesh cylinder 1008.

The diameter of each mesh cylinder 1008 can be changed by axially moving the ends of the mesh cylinder relative to each other (i.e., an axial length of the mesh cylinders can be shortened or lengthened) by pushing or pulling on mandrel 1011. For example, one end of a mesh cylinder can move towards the other end using mandrel 1011 to cause the mesh cylinder to expand and one end of the mesh cylinder can move away from the other end using mandrel 1011 to cause the mesh cylinder to contract. Mandrel extends between the mesh cylinder 1008 and a control rod 1033 located at proximal end 1004 of device 1000. Although FIG. 10 illustrates control rod 1033 not in communication with controller 1010 and, for example manually operated, such embodiments where it is in communication with controller 1010 are possible.

In one embodiment, device 1000 can include both a mandrel 1011 and a sheath 1009. While the use of just a mandrel will allow expansion and contraction of a single element and just a sheath will allow expansion and contraction of a single element or expansion and contraction of both element to be performed together, using a combination of mandrel 1011 and sheath 1009 or using as many mandrels as there are cylinders allows for the expansion and contraction of each distendable element to be accomplished independently. For example, while one of the distendable elements is controlled by the mandrel, the other of the distendable elements can be controlled by a sheath. In this example the distendable element controlled by the mandrel will expand and contract by axially moving the ends of the element together or apart. The other of the distendable elements can be a self-expanding element that expands upon sliding the sheath that surrounds the element away. As illustrated in FIG. 10, sheath 1009 extends between a mesh cylinder 1008 and a sheath control 1035 located at proximal end 1004 of device 1000. Although FIG. 10 illustrates sheath control 1035 not in communication with controller 1010 and, for example, manually operated, such embodiments where it is in communication with controller 1010 are possible.

Sections of each mesh cylinder or distendable element 1008 can be covered by a non-conductive polymer layer to allow for more uniform distension in focal areas. Areas of a conductive mesh not insulated by the polymer layer could serve as the contact point for electrodes used to electrically stimulate the walls of the compartment. In addition, the distension surface of the mesh cylinders 1008 can be textured to provide mucosal irritation, which can stimulate neurons during the normal process of peristalsis in a GI tract. In addition, the surface of the mesh can also be coated with a drug polymer matrix that is capable of providing hormonal stimulation.

Figure 11:
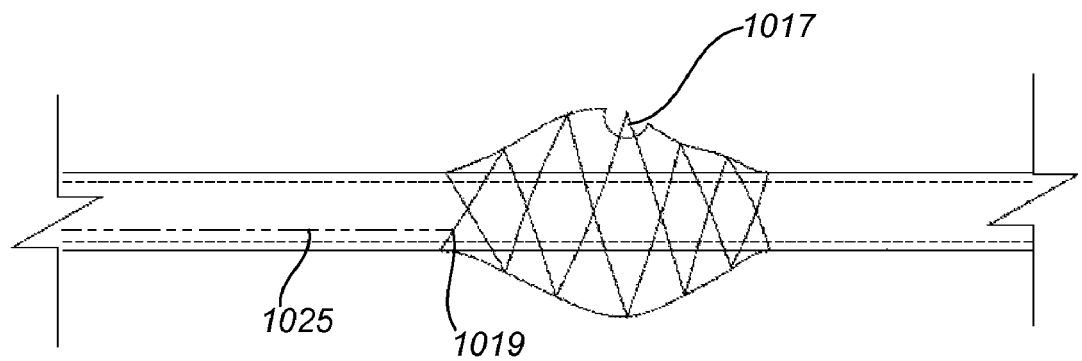
FIG. 11 is an enlarged schematic diagram of an exposed metallic mesh that provides electrical stimulation in one embodiment of the FIG. 10 device.

Device 1000 also includes at least one electrical component in contact with each of the distendable elements 1008. The at least one electrical component is configured to repeatedly activate and deactivate electrical stimulation to the select body tissues and organs of a compartment. The at least one electrical component can also be configured to sense electrical activity of the compartment, such as GI electrical activity. In the FIG. 10 embodiment, device 1000 can include cathode electrode 1012 and anode electrode 1014 disposed along the outer surface of each mesh cylinder 1008. However, in the case of metallic mesh cylinders, the electrode components can be created by exposing metallic members 1017 of each mesh as shown in FIG. 11 and making an electrical connection 1019 between an electrode lead 1025 and the mesh.

Electrodes 1012 and 1014 are in communication with controller 1010 via electrical leads that run from electrodes 1012 and 1014 to a multi-pin electrical connector 1027, which is coupled to proximal end 1004 of tube 1002. Electrical leads are illustrated and described in more detail in the sectional view of tube 1002 in FIG. 12.

Like device 800, device 1000 includes a plurality of outlets 1016 located along the sides of the tube 1002 proximate distal end 1006 as well as at distal end 1006 for the evacuation and delivery of fluids and solids into the compartment. In an alternative embodiment, an outlet can be located just at distal end 1006 or outlets can be located just along the side proximate distal end 1006. Although not particularly illustrated in FIG. 10, additional or alternative outlets other than the outlets 1016 shown in FIG. 10 can be included in device 1000. For example, outlets can be located proximal, in between and/or distal to the distendable elements 1008. Locations of outlets can vary depending on the intended anatomical location of tube 1002 and the portion or portions of the compartment or GI tract that requires evacuation as will be discussed in detail in FIGS. 17 and 18.

Figure 12:
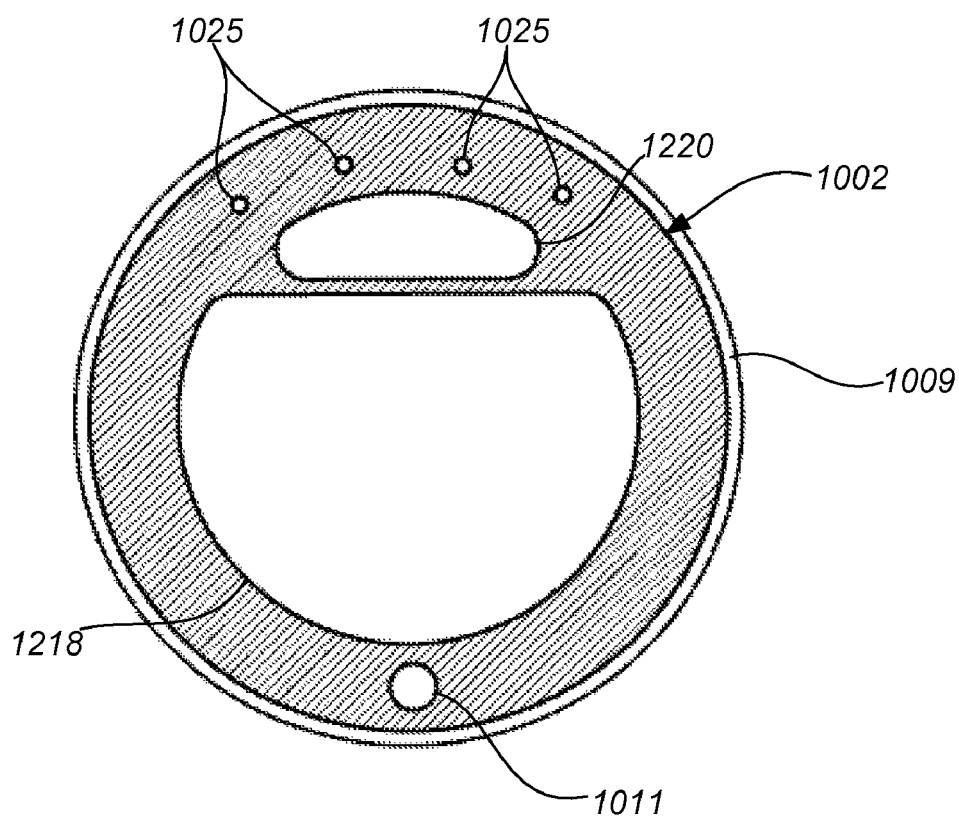
FIG. 12 is a sectional view of a tube of the device illustrated in FIG. 10.

FIG. 12 illustrates a sectional view of tube 1002 of device 1000. As illustrated, tube 1002 is a multi-lumen flexible tube and in one embodiment can include removable sheath 1009 that surrounds tube 1002 and mandrel 1011 that can move ends of the distendable elements together or away from each other. At least one lumen or primary lumen 1218 of tube 1002 is of a sufficient diameter to function for the evacuation and delivery of fluids and solids, such as a hormonal stimulant. A secondary lumen 1220 acts as a vent or flush port. Primary lumen 1218 and secondary lumen 1220 extend from at least one of the outlets 1016 of device 1000 to connect to connectors located at proximal end 1004 (not illustrated in FIG. 10). In one embodiment, primary lumen 1218 can be coupled to controller 1010. However, in other embodiments, primary lumen 1218, like secondary lumen 1220 need not be controlled by controller 1010.

Tube 1002 also includes electrical leads 1025 that provide electrical energy to electrodes 1012 and 1014 that are in contact with the distendable elements. In FIG. 12, tube 1002 includes four electrical leads 1025, one for each of two cathode-type electrodes 1012 and one for each of two anode-type electrodes 1014. However, leads 1025 can also couple to exposed metallic mesh of distendable elements 1008 as illustrated in FIG. 11. Electrical leads 1025 travel from their connections to distendable elements 1008 to an external connector 1027 that is coupled to controller 1010. It should be realized that tube 802 can include any number of electrical leads 1025.

Figure 13:
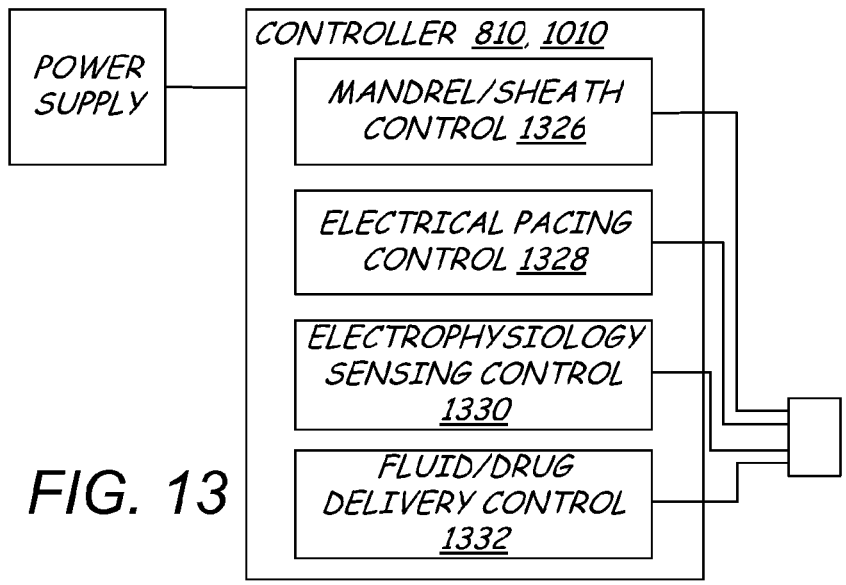
FIG. 13 is a block diagram of a controller of the devices illustrated in FIGS. 8A, 8B and 10.

FIG. 13 illustrates a block diagram of controllers 810 and 1010 illustrated in FIGS. 8 and 10. Controllers 810 and 1010 include an optional mandrel/sheath control 1326, an electrical pacing control 1328, an electrophysiological sensing control 1330 and an optional fluid/drug delivery/suction control 1332. Controller 810, 1010 is powered by a power supply as illustrated. Mandrel/sheath control 1326 operates to actuate a mandrel 1011 and/or a sheath 1009 to expand or contract distendable elements. In an alternative embodiment, the expansion and contraction of distendable elements using mandrel 1011 and/or sheath 1009 can be manually performed without the use of controller 810 and 1010. Electrical pacing control 1328 operates to provide electrical energy through electrical leads 925, 1025 for controlled activation and deactivation of electrodes when electrical pacing control 1328 is controlling devices 800 and 1000.

Electrophysiological sensing control 1330 operates to gather data related to sensing of a compartment when electrodes also function to sense activity in the compartment. For example, when the compartment is a GI tract, electrodes can sense gastrointestinal activity. Fluid/drug delivery/suction control 1332 provides and evacuates fluids and solids, such as hormonal stimulant, to and from the compartment through primary lumen 918 and 1218. Again, control 1332 could be eliminated and fluid/drug delivery/suction can occur with some other means. Through primary lumen 918 and 1218, control 1332 can feed and administer drugs and other oral agents by either supplying minimal amounts of oral fluids or supplying a continuous stream of oral fluids. Through primary lumen 918 and 1218, control 1332 can also aspirate or drain the contents in the compartment, such as aspirate or drain gastric secretions or swallowed air.

FIG. 14A illustrates a device 1400 for stimulating select body tissues and organs in a compartment under another embodiment. As discussed above, although device 1400 will be discussed as being useful in a GI lumen, it should be understood that the device 1400 can be useful in other lumens in a body.

Figure 14B:
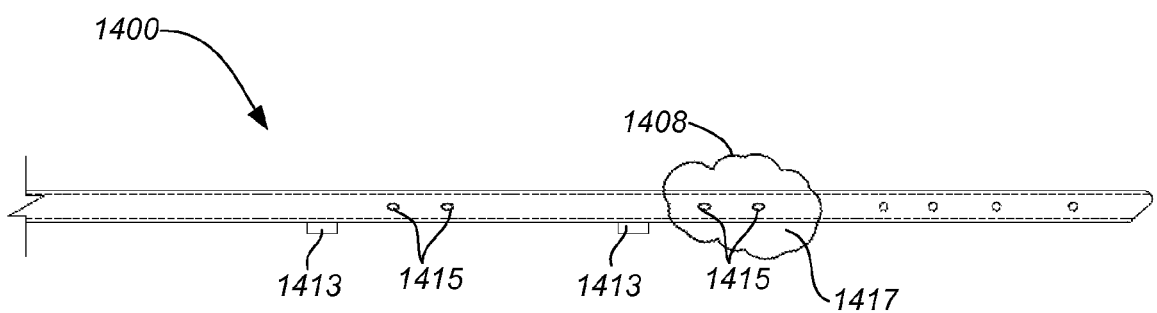
FIG. 14B is an enlarged schematic diagram of a portion of the device illustrated in FIG. 14A.

Device 1400 is similar to device 500 in that it includes a tube or catheter 1402 having a proximal end 1404 and a distal end 1406 and at least one distendable element 1408 coupled to and located along tube 1402. The at least one distendable element 1408 is in closer proximity to distal end 1406 than proximal end 1404. Unlike device 500, distendable element 1408 is conducting gel 1417 that is dispensed out of pores 1415 located in tube 1402 as illustrated in FIG. 14B. Conducting gel 1417 is repeatedly dispensed out of pores 1415 and then evacuated from within the compartment. Placing conducting gel 1417 into a first position by dispensing the conducting gel expands the walls of the compartment at the point where pores 1415 are located. Placing conducting gel 1417 into a second position by evacuating the conducting gel contracts the walls of the compartment at the point where pores 1415 are located. Although device 1400 includes two areas of pores 1415 for dispensing conducting gel, it should be realized that a single or any number of areas of pores 1415 can be used.

Pores 1415 can be in communication with a controller 1410 via connectors 1437, which are coupled to proximal end 1404 of tube 1402. Conducting gel 1417 from the different areas of pores 1415 can be dispensed independently or in a time-related fashion as determined by controller 1410 and, although not specifically illustrated in FIG. 14, conducting gel can also be dispensed at the same time by controller 1410.

Besides conducting gel 1417 distending the compartment, dispensed conducting gel can also act as an electrical component or electrode of device 1400 to repeatedly activate and deactivate electrical stimulation to the select body tissues and organs of the compartment. Examples materials for a conductive gel electrode are discussed in the FIG. 5 description.

To assist conducting gel 1417 in electrical stimulation, pores 1415 are also in communication with controller 1410 via electrical leads that run from pores 1415 to an electrical connector 1427 located at proximal end 1404 of device 1400. Electrical leads are illustrated and described in more detail in the sectional view of tube 1402 in FIG. 15. In addition, device 1400 includes ground electrodes 1413 for the current return path when electrical stimulation occurs via conducting gel 1417. However, it is possible to eliminate electrodes 1413 by using conducting gel for a return path as is used in the FIG. 5 embodiment.

Like device 500, device 1400 also includes a plurality of outlets 1416 located along the sides of the tube proximate distal end 1406 as well as at distal end 1406 for the evacuation and delivery of fluids and solids, such as hormonal stimulant into the compartment. In an alternative embodiment, a single outlet can be located at distal end 1406 or outlets can be located along the side proximate distal end 1406. Although not particularly illustrated in FIG. 14A, additional or alternative outlets other than the outlets 1416 shown in FIG. 14A can be included in device 1400. For example, outlets can be located proximal, in between and/or distal to the distendable elements 1408. Locations of outlets can vary depending on the intended anatomical location of tube 1402 and the portion or portions of the compartment or GI tract that requires evacuation as will be discussed in detail in FIGS. 17 and 18.

Like tube 502, tube 1402 can optionally include a sheath (not illustrated). During insertion, the sheath can cover the entire outer surface of tube 1402 including pores 1415 and the portion of tube 1402 that includes outlets 1416 to protect the pores or to protect the GI tract from device 1400. After insertion, the sheath can be retracted to expose pores 1415 for stimulating the GI tract.

Figure 15:
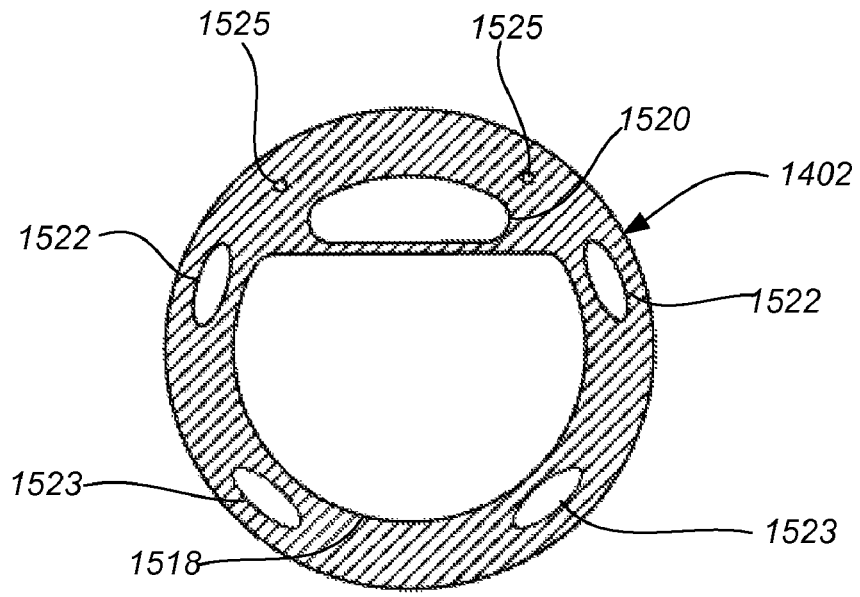
FIG. 15 is a sectional view of a tube of the device illustrated in FIG. 14A.

FIG. 15 illustrates a sectional view of tube 1402 of device 1400. As illustrated, tube 1402 is a multi-lumen flexible tube. At least one lumen or primary lumen 1518 of tube 1402 is of a sufficient diameter to function for the evacuation and delivery of fluids and solids, such as hormonal stimulant. A secondary lumen 1520 acts as a vent or flush port. Primary lumen 1518 and secondary lumen 1520 extend from at least one of the outlets 1416 of device 1400 to connect to connectors located at proximal end 1404 (not illustrated in FIG. 14A). In one embodiment, primary lumen 1518 can be coupled to controller 1410. However, in other embodiments, primary lumen 1518, like secondary lumen 1520, need not be controlled by controller 1410.

Tube 1402 also includes tertiary lumens 1522 and 1523 for dispensing and evacuating conducting gel through pores 1415 to expand and contract the walls of a compartment and for activating and deactivating electrical stimulation. Although conducting gel could be supplied to and evacuated from the same pores 1415 using only as many lumens as there are areas of distension on tube 1402, such through two tertiary lumens 1522, conducting gel could be supplied to some of pores 1415 using lumens 1522 and evacuated from other of the pores 1415 using lumens 1523. Electrical leads 1525 provide electrical energy to conducting gel 1417 and pores 1417. In addition, other leads can be included in tube 1402 to for connection to ground electrodes 1413.

Figure 16:
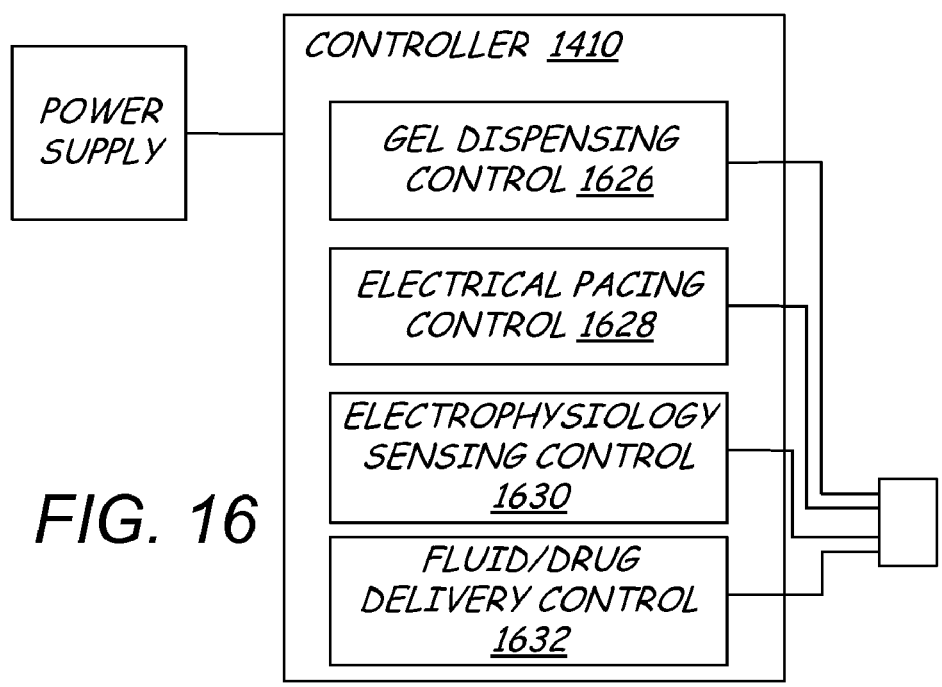
FIG. 16 is a block diagram of a controller of the device illustrated in FIG. 14A.

FIG. 16 illustrates a block diagram of controller 1410 illustrated in FIG. 14. Controllers 1410 include conducting gel dispensing control 1626, an electrical pacing control 1628, an electrophysiological sensing control 1630 and an optional fluid/drug delivery/suction control 1632. Gel dispensing control 1626 operates to provide conducting gel through tertiary lumens 1522 (FIG. 4) for controlled dispensing to pores 1415 in device 1400 and through lumens 1522 or 1524 for controlled evacuation through pores 1415. In an alternative embodiment, the dispensing and evacuation of conducting gel can be manually performed without the use of controller 1410. Electrical pacing control 1628 operates electrical lead 1525 for the activation and deactivation of electrical energy.

Electrophysiological sensing control 1630 operates to gather data related to sensing of a compartment when electrodes (not illustrated in FIG. 14, 15 or 16) function to sense activity in the compartment. For example, when the compartment is a GI tract, electrodes can sense gastrointestinal activity. Fluid/drug delivery/suction control 1632 provides and evacuates fluids and solids to and from the compartment through primary lumen 1518. Again, control 1632 could be eliminated and fluid/drug delivery/suction can occur with some other means. Through primary lumen 1518, control 1632 can feed and administer drugs and other oral agents by either supplying minimal amounts of oral fluids or supplying a continuous stream of oral fluids. Through primary lumen 1518, control 1632 can also aspirate or drain the contents in the compartment, such as aspirate or drain gastric secretions or swallowed air.

Figure 17:
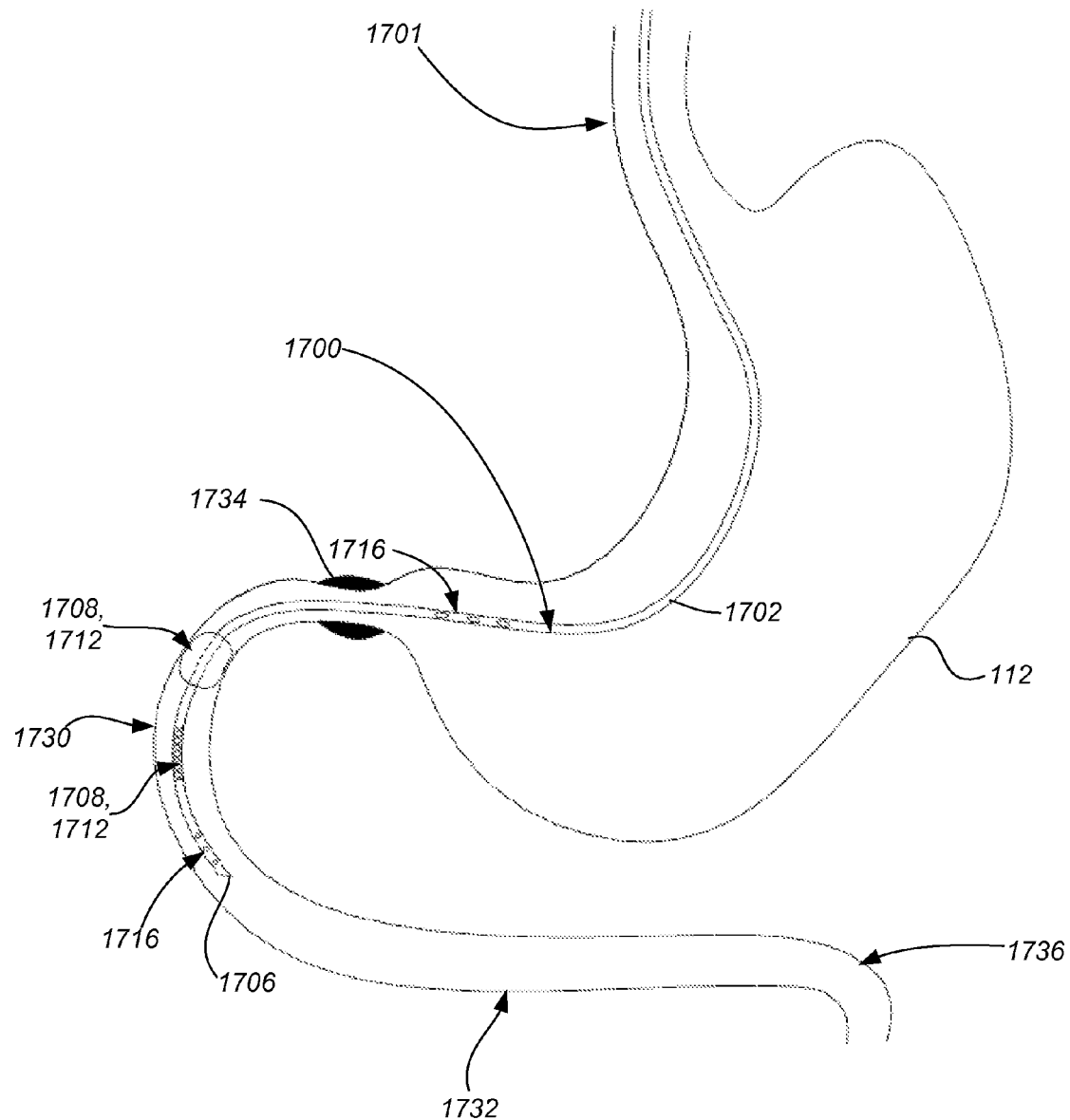
FIG. 17 illustrates a first placement of one of the devices illustrated in FIGS. 2-3, 5, 8A-8B, 10 and 14A-14B in a gastrointestinal tract.
Figure 18:
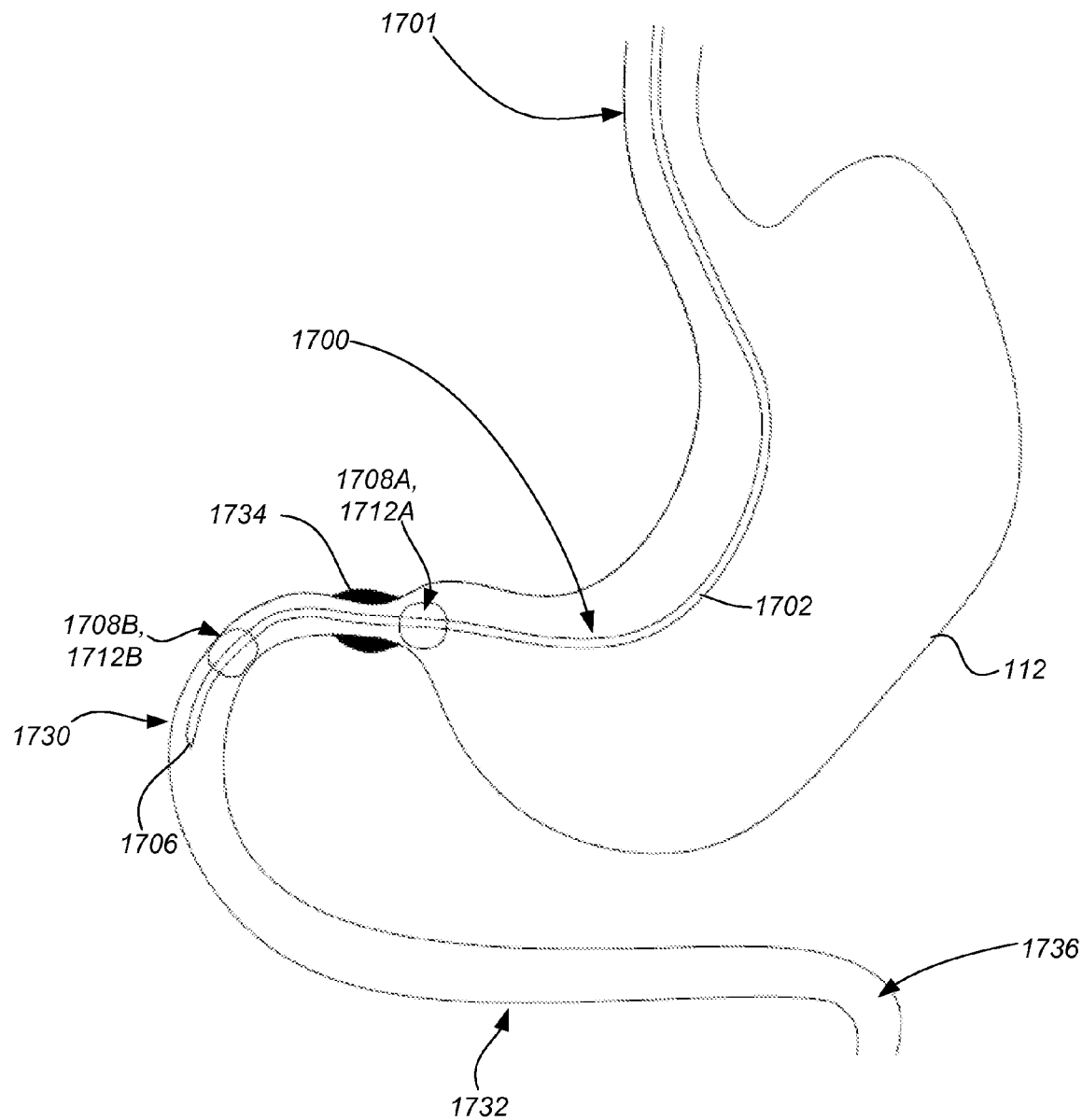
FIG. 18 illustrates a second placement of any of the devices illustrated in FIGS. 2-3, 5, 8A-8B, 10 and 14A-14B in the gastrointestinal tract.

FIGS. 17 and 18 illustrate placements of a device 1700 in a compartment, such as a GI tract 1701. For the following discussion of device placement, the active portions of the tube are considered, including but not limited to the electrical and mechanical stimulation components 1712 and 1708 and the outlets 1716 of the primary lumen. From FIGS. 17 and 18 it can be seen that an additional portion of device 1700 will necessarily occupy space between the opening (or mouth 106 illustrated in FIG. 1) of the GI tract 1701 to an anatomical location of the active portion of device 1700.

Placement of the active elements of device 1700 can be anywhere in the GI tract 100, from the esophagus 110 (FIG. 1) to the rectum 118 (FIG. 1). Placement can be such that the device occupies multiple distinct anatomical locations within the tract, for example it can be placed so that it crosses the esophageal sphincter 120 (FIG. 1) and can apply stimulation to both the esophagus 110 and stomach 112 (FIGS. 1, 17 and 18), or it can be placed so that it crosses the pyloric sphincter 122 (FIG. 1) and can apply stimulation to the stomach and the duodenum (the first portion of the small intestine coupled to the stomach). Other placements for achieving stimulation are possible. Active portions of device 1700 can also be such that the suction/evacuation function of the device occurs near the same area as stimulation, or that evacuation and stimulation occur at distinct locations. For example, the device could be placed so that it crosses the pyloric sphincter 122 (FIG. 1) with the suction/evacuation ports located in the stomach 112 and the stimulation components located in the duodenum.

FIG. 17 illustrates a first possible position of device 1700 in GI tract 100. Tube 1702 is inserted through mouth 106 through the compartment or GI tract 100 and into the proximal duodenum 1730 and duodenum 1732 so that the distendable elements 1708 of the device (be they balloons, mesh cylinders or conducting gel dispensed from pores) are past the pylorus 1734 without extending past the ligament of Treitz 1736. Outlets 1716 for evacuation or fluid administration can be located at distal end 1706 of the device 1700 or anywhere along its length, such as in the stomach 112 as also illustrated.

Placement of the active portion of device 1700 in the esophagus 102 (FIG. 1), or crossing the esophageal sphincter 120 (FIG. 1) could be used for the treatment of gastroesophageal reflux disease (GERD). Placement of the active portion of device 1700 in the stomach 112 could be used to treat gastroparesis, or conversely a different stimulation regime could be used to slow gastric emptying for the treatment of obesity. Placement of the active portion of device 1700 in the stomach and across the pyloric sphincter 122 (FIG. 1) into the duodenum 1732 could be used to promote normal GI tract function to treat postoperative ileus or gastroparesis, or as previously mentioned could be used to disrupt normal GI function to slow gastric emptying and treat obesity. Placement of the active portion of device 1700 solely in the duodenum 1732 could also be used to stimulate normal gastrointestinal motility or could be used to slow gastric emptying for the treatment of obesity. Placement of the active portion of device 1700 in the colon or large intestine 114 (FIG. 1) could be used to treat constipation or diarrhea. The active portion of device 1700 could also be placed at varying locations in the modified anatomy of gastrointestinal surgery patients, for example those that have had gastric bypass surgery or some other gastrointestinal surgical procedures.

Alternatively, as shown in FIG. 18, the active portion of device 1700 can be placed so that one of the mechanical/electrical stimulation segments 1708A and 1712A located along tube 1702 is above the pylorus 1734, in the stomach 112, so that stimulation begins in the stomach, crosses the pylorus, and is continued in the proximal duodenum 1730 with another stimulation segment 1708B and 1712B. Evacuation/administration outlets can be located at the distal end 1706 and/or along the distal sides of the tube. Location of outlets at distal end 1706 that communicate with the space at a proximal end of tube 1702 and used for the evacuation of GI contents are chosen so that evacuation of the bowel and stomach can be accomplished regardless of the placement of the active portions of device 1700 in the duodenum 1730, in the stomach 112 and duodenum 1730, or entirely in the stomach 112.

While the preceding paragraphs discuss the placement of device 1700 for the application of therapy, device 1700 could also be used as a diagnostic tool for assessing function of the GI tract. Proper placement of the device into the esophagus 110 (FIG. 1), stomach 112 (FIG. 1), or small 114 (FIG. 1) or large intestines 116 (FIG. 1), and rectum 118 (FIG. 1) would allow clinicians to use the sensing electrodes to detect gastric myoelectrical activity. The mechanical distendable devices could be expanded and the pressures monitored to detect the muscular contractions of the GI tract. In addition, the GI tract could be stimulated (either electrically or mechanically) and its response monitored using device 1700.

Device 1700 can be placed or inserted into a GI tract for varying durations depending on the intended use. For example, it may be in place less than an hour or for just a few hours for diagnostic purposes. For the treatment or prevention of postoperative ileus the device may be in place for hours or days. For the treatment of chronic gastric disorders or obesity, the device may be placed for extended durations ranging from a week to a month or several months. As previously discussed, besides placing or inserting device 1700 in a gastrointestinal tract, device 1700 can be placed in any lumen, compartment, and passageway of the body. More specifically, device 1700 can be positioned in any portion of the GI tract including the esophagus, gastroesophageal junction, stomach, gastrointestinal junction, small intestines, large intestines, colon and rectum.

For the treatment of esophageal disorders, device 1700 can be positioned along the esophagus and gastroesophageal junction. For the treatment of gastric disorders, device 1700 can be positioned in the stomach and gastrointestinal junction. For the treatment of intestinal motility disorder, device 1700 can be positioned in the small and large intestine. For rectal disorders, device 1700 can be positioned in the rectum. Device 1700 may be used to modulate any mechanoreceptor and baroreceptor in an intraluminal and extraluminal compartment and passageway.

Device 1700 can be used to modulate any secretory organ or gland with mechanical distention and electrical stimulation. For example, device 1700 can supply mechanical and electrical stimulation of the mechanical and/or baroreceptors (i.e. arterial wall, carotid sinus, baroreceptors, chemoreceptors, aorta) to modulate blood pressure. Device 1700 can also modulate hormonal release and response in these types of organs. In another example, mechanical and/or electrical stimulation of the thyroid gland can modulate thyroid function for the treatment of thyroid disorders. In another example, mechanical distention of the distendable elements of device 1700 can be combined with electrical stimulation at higher frequencies to cauterize & ablate tissue thus aiding in coagulation and homeostasis. In yet another example, device 1700 can be placed around a lumen to mechanically compress and electrically stimulate (compress vessel, stomach, esophagus, thyroid, bladder, etc.). In still another example, mechanical distention and electrical stimulation of the GI tract using device 1700 can simulate feeding state which modulates (up-regulates, stimulates) insulin secretion for the treatment of diabetes. In further examples, mechanical distention and electrical stimulation may be used for the treatment of rectal and vaginal prolapse, used to treat chronic pain syndrome by stimulating the spinal cord, nerve roots and nerves, and dorsal column to modulate pain perception and release endorphins, used to treat esophageal varices (the balloon tamponades the varices and the electrical stimulation cauterize/coagulates it from bleeding), used to treat epistaxis (balloon tamponades nose bleed and the electrical stimulation cauterize/coagulates the tissues to stop bleeding) and used to treat choanal atresia by dilating and electrically stimulating/cauterizing intranasal/sinus tissue.

FIGS. 19-24 illustrate graphical representations of a variety of different schemes in regards to the coordination of applied mechanical stimulation using distendable elements with applied electrical stimulation using electrical energy for the devices illustrated in FIGS. 2-3, 5, 8, 10, 14 and 17-18. In FIGS. 19-24, Waveform A represents the underlying amplitude of myoelectrical activity sensed at a location in a GI tract or other type of compartment in the body over time. This activity is sensed by sensing electrodes, or by the stimulation electrodes when not stimulating. Waveform B represents the amplitude of applied mechanical distension on distendable elements of a device. The beginning of each pulse in waveform B represents the expansion of a distendable element and the end of each pulse in waveform B represents the contraction of the distendable element. Waveform C represents the amplitude of electrical pacing stimulation applied via electrodes or other type of conductive material. The beginning of each pulse in waveform C represents the activation of electrical energy and the end of each pulse in waveform C represent the deactivation of electrical energy. The ultimate goal in applying mechanical and electrical stimulation is to provide a sufficient input to the excitatory motor neurons in the GI tract or other type of compartment in the body to trigger a propulsive contraction of the smooth muscle.

Figure 19:
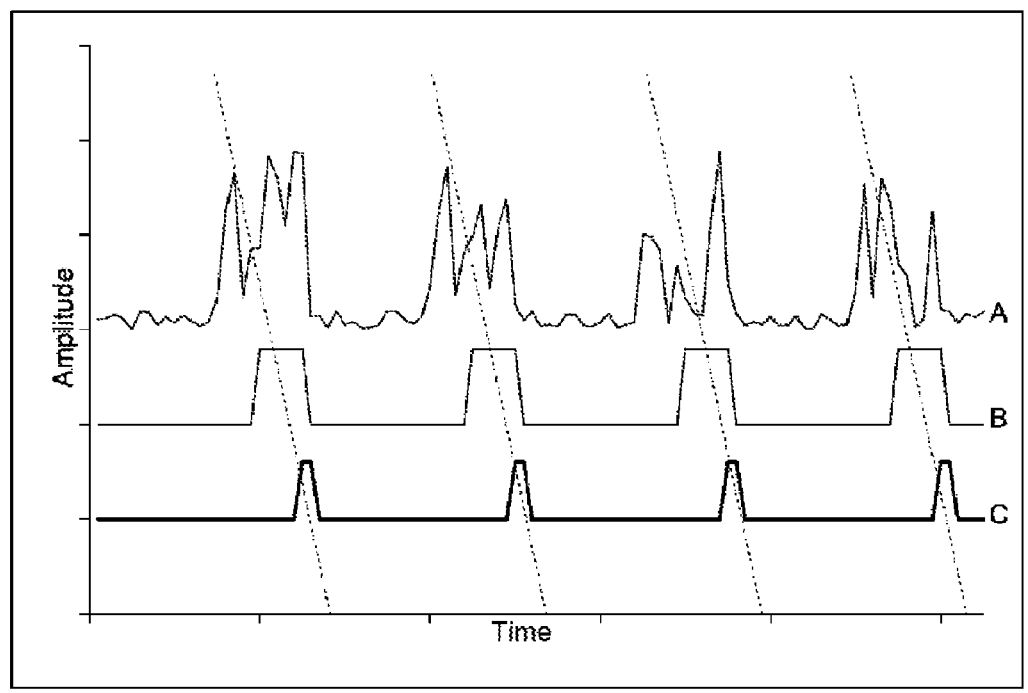
FIGS. 19-24 illustrate graphical representations of the synchronization of application of mechanical and electrical stimulation in the compartment.

In one embodiment and as illustrated in FIG. 19, myoelectrical activity in a GI tract can include slow waves as illustrated in groups of pulses in waveform A. Under these circumstances, the application or pulse of mechanical distention (waveform B) is timed to occur just after each slow wave of myoelectrical activity (waveform A) that is sensed. The application or pulse of electrical pacing stimulation (waveform C) is timed to occur just after the application of mechanical distention. It should be realized that the initiation of the electrical stimulation can take place while the mechanical distension is still completing its cycle of expansion and contraction (i.e., pulse) or the initiation of the electrical stimulation can take place after the mechanical distension has completed its cycle of expansion and contraction. Alternatively, the order of the mechanical and electrical stimulation may be reversed. For example, electrical pacing stimulation can occur just after myoelectrical activity is sensed and then the application of mechanical distention can be applied just after the application of electrical stimulation.

Figure 20:
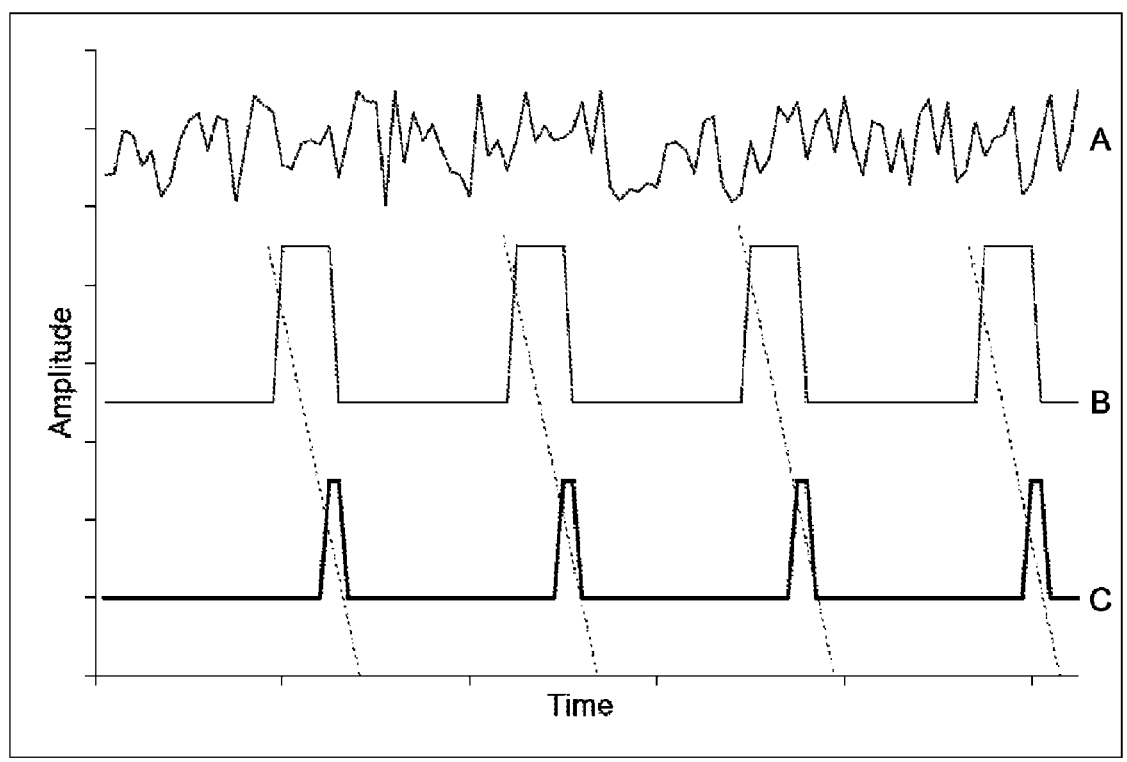

In another embodiment and as illustrated in FIG. 20, instead of myoelectrical activity (waveform A) having slow waves, the myoelectrical activity can be disorganized with no discernible slow waves being present. Under these circumstances, the mechanical distention (waveform B) occurs at a given frequency and the electrical stimulation (waveform C) is timed to occur after the initiation of expansion of the mechanical distention. In other words, electrical stimulation frequency is based on the given mechanical distention frequency, where electrical stimulation occurs just after mechanical distention is applied. In this embodiment, mechanical distension frequency is chosen without considering myoelectrical activity. It should be realized that the initiation of the electrical stimulation can take place while the mechanical distension is still completing its cycle of expansion and contraction (i.e., pulse) or the initiation of the electrical stimulation can take place after the mechanical distension has completed its cycle of expansion and contraction (i.e., pulse).

Figure 21:
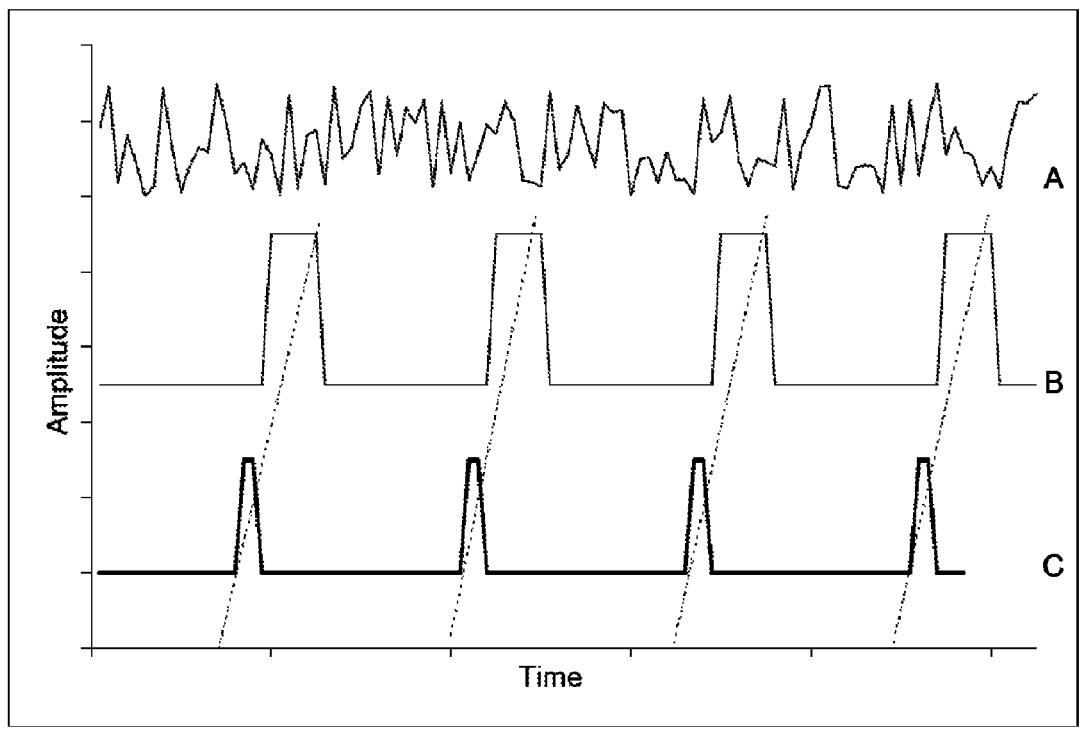

In yet another embodiment and as illustrated in FIG. 21, when disorganized myoelectrical activity (waveform A) exists, in the alternative, the electrical stimulation (waveform C) can occur at a given frequency and the mechanical stimulation (waveform B) occurs after initiation of activation of the electrical stimulation. In other words, mechanical distention frequency is based on the given electrical distention frequency, where mechanical distention occurs just after electrical stimulation is applied. It should be realized that the initiation of the mechanical stimulation can take place while the electrical stimulation is still completing its cycle of activation and deactivation (i.e., pulse) or the initiation of the mechanical stimulation can take place after electrical stimulation has completed its cycle of activation and deactivation.

Figure 22:
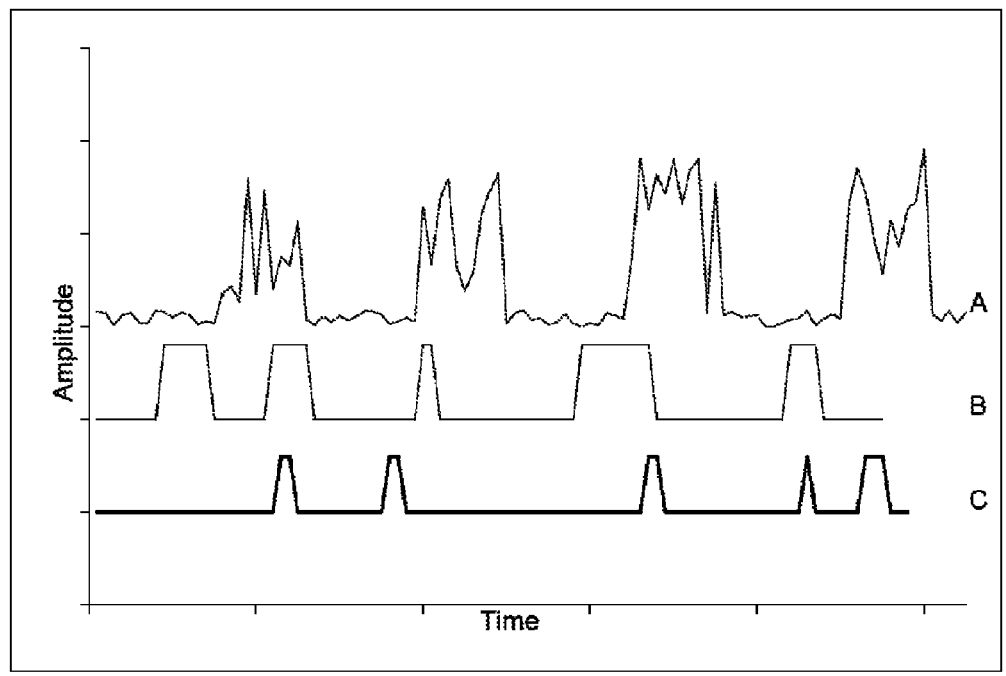

In still a further embodiment and as illustrated in FIG. 22, mechanical stimulation (waveform B) and electrical stimulation (waveform C) can be applied in a random fashion during normal myoelectrical activity (waveform A). Such a stimulation scheme could be applied to disrupt normal GI tract activity to slow gastric emptying for the treatment of obesity. Alternatively, stimulation applied in response to normal gastric myoelectrical activity, but applied in such a fashion as to stimulate retrograde peristalsis could also be applied. A third possibility for the treatment of obesity is the application of noxious mechanical and/or electrical stimuli to diminish normal GI tract motility. Mechanical distention and/or electrical stimulation can provide a sensation of fullness and satiety for the treatment of obesity.

Figure 23:
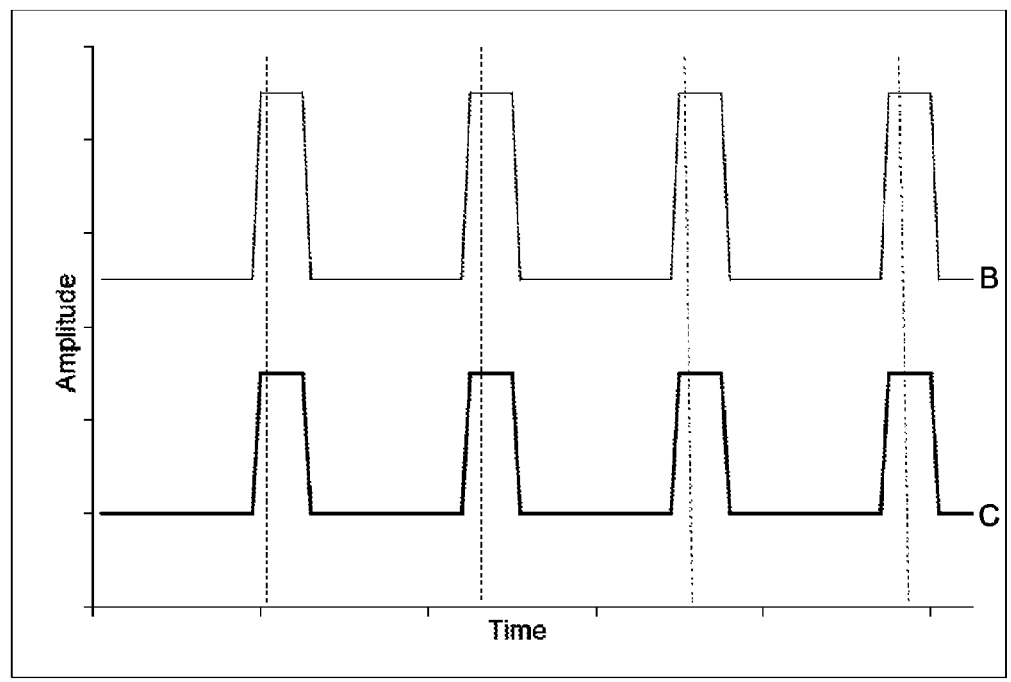
Figure 24:
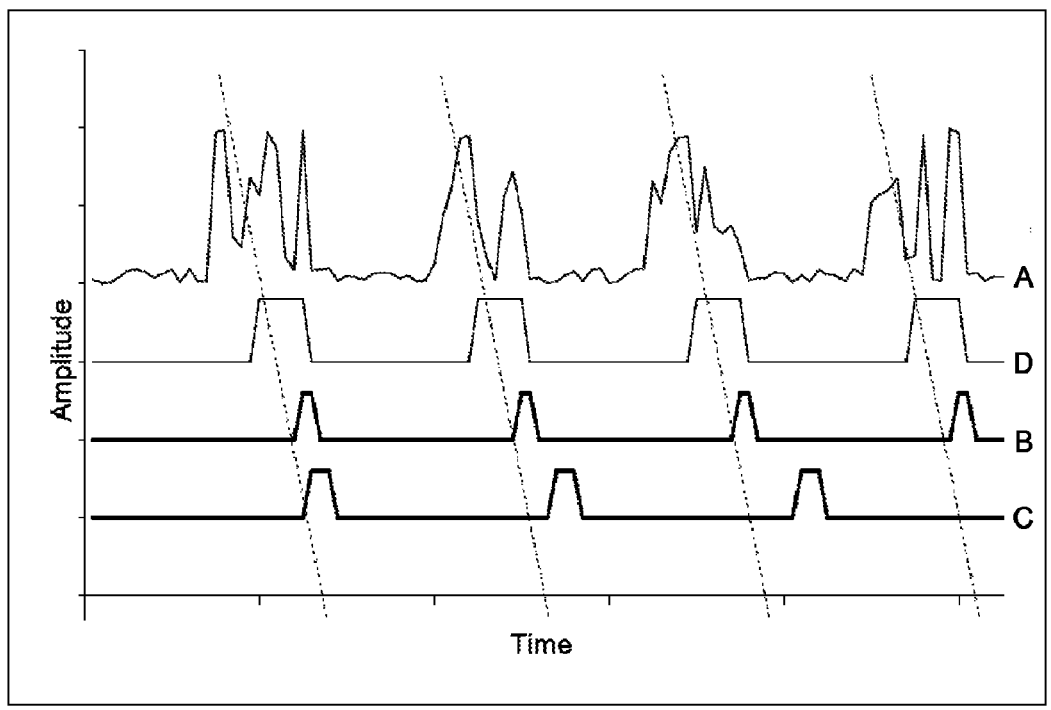

In still further embodiments, FIG. 23 shows mechanical stimulation (waveform B) occurring synchronously with electrical stimulation (waveform C). This synchronous application can be applied in the case where myoelectrical activity is a slow wave as illustrated in FIG. 19 or disorganized as illustrated in FIGS. 20 and 21. FIG. 24 illustrates the addition of hormonal stimulation (waveform D), for example by the administration of a liquid foodstuff, followed by mechanical stimulation (waveform B), which is then followed by electrical stimulation (waveform C) during slow wave myoelectrical activity (A). Of course, hormonal stimulation can be coordinated with mechanical stimulation and electrical stimulation in other embodiments following a slow wave or pulse of myoelectrical activity or following disorganized myoelectrical activity.

It should be understood that any sequence of sensing, mechanically stimulating, electrically stimulating, and/or humorally stimulating could be used depending on the desired outcome. In addition, the time between different stimulation modalities can range from less than a second to multiple hours. For example, a number of mechanical stimulations could be administered for minutes or hours, and then a number of electrical stimulations could be applied for the next time period. Discrete stimulation modules (a module, for example, could be a single balloon instrumented with electrodes) can also provide stimulation simultaneously, in a phased fashion, or asynchronously, depending on the desired response. It should also be understood that for the treatment of obesity or to impair gastric emptying, the application of only mechanical distention (without electrical stimulation) of sufficient force to cause inhibitory stimulation of the GI tract is also possible.

The parameters for using electrical stimulation differ slightly depending on what portion of the GI tract is being stimulated. In or around the stomach, electrical energy can be applied at an amplitude between 0 and 10 mA for 2 to 15 pulses per minute. In or around the small intestine, electrical energy can be applied at an amplitude between 0 and 10 mA for 10 to 40 pulses per minute. In or around the large intestine, electrical energy can be applied at an amplitude between 5 and 40 mA for 10 to 50 Hz.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A device for stimulating select body tissues and organs from within a compartment in a body, the device comprising:
   a tube having a distal end, a proximal end and a plurality of lumens, the tube positionable into the compartment of the body;
   at least one distendable element located along and coupled to the tube in closer proximity to the distal end than to the proximal end, each distendable element configured to provide a sequence of pulses against the select body tissues and organs within the compartment over a period of time, wherein each pulse of the distendable element comprises expansion of the distendable element into a first position and contraction of the distendable element into a second position; and
   at least one electrical component in association with each of the distendable elements and configured to provide a sequence of pulses to the select body tissues and organs in the compartment over the select time period, wherein each pulse of the electrical component comprises an activation of the electrical energy and a deactivation of electrical energy.

2. The device of claim 1, wherein the compartment comprises a gastrointestinal tract.

3. The device of claim 1, wherein each distendable element expands into the first position and contracts into the second position by independent operations separate from each other.

4. The device of claim 1, wherein the at least one distendable element comprises a plurality of distendable elements located along and coupled to the tube, wherein the pulses of the distendable elements substantially simultaneously expand into the first position and substantially simultaneously contract into the second position.

5. The device of claim 1, wherein the at least one distendable element comprises first and second distendable elements, wherein of the first distendable element is located closer to the distal end of the tube and the second distendable element is located closer to the proximal end of the tube, wherein at a set period of time the pulse of the first distendable element is expanded into the first position and the pulse of the second distendable is contracted into the second position.

6. The device of claim 1, wherein each distendable element comprises a balloon inflatable by a fluid fed through one of the plurality of lumens in the tube that is supplied outside the compartment.

7. The device of claim 1, wherein each distendable element comprises a self-expanding element, wherein each distendable element is actuated from the first position into the second position with a constraining component that slides along the tube.

8. The device of claim 1, wherein each distendable element radially expands into the first position by moving ends of each element together with a mandrel and each distendable element radially contracts into the second position by moving the ends of each element apart with the mandrel.

9. The device of claim 1, wherein the at least one distendable element comprises a pair of distendable elements, one of the pair of distendable elements comprises a self-expanding element that is actuated from the first position into the second position with a constraining component that slides along the tube while the other of the pair of distendable elements radially expands into the first position by moving ends of each element together with a mandrel and each distendable element radially contracts into the second position by moving the ends of each element apart with the mandrel.

10. The device of claim 1, wherein the at least one distendable element comprises a gel configured to dispense through pores in the tube to distend the select body tissue and organs.

11. The device of claim 1, wherein the at least one electrical component that is in association with each of the distendable elements comprises at least one electrode placed on an outer surface of each distendable element.

12. The device of claim 11, wherein the at least one electrode comprises a coiled or ribboned electrode that is wound about the at least one distendable element.

13. The device of claim 1, wherein the at least one electrical component comprises a conductive gel configured to dispense through pores in the tube to provide electrical stimulation.

14. The device of claim 1, further comprising a controller coupled to the proximal end of the tube and configured to control the expansion and contraction of the at least one distendable element and configured to control the activation and deactivation of the at least one electrical component.

15. The device of claim 1, wherein one of the plurality of lumens includes an outlet location along the tube, the lumen provides a hormonal stimulant to the compartment at the location of the outlet.

16. A method of non-invasively treating select body tissues and organs from within a compartment in a body, the method comprising:
    providing a multi-lumen tube having at least one distendable element and at least one electrical component in contact with each of the distendable elements along a length of the tube;
    inserting the tube within the compartment of the body;
    mechanically stimulating the compartment in the body by sequentially pulsing the at least one distendable element against a portion of the compartment, each pulse comprising expanding the at least one distendable element into a first position and contracting the at least one distendable element into a second position; and
    electrically stimulating the compartment in the body by sequentially pulsing the at least one electrical component, each pulse comprising activating the at least one electrical component and deactivating the at least one electrical component.

17. The method of claim 16, further comprising sensing myoelectrical activity in the compartment using the at least one electrical component.

18. The method of claim 17, further comprising:
    initiating each pulse of the at least one distendable element after an occurrence of a waveform of the sensed myoelectrical activity; and
    initiating each pulse of the at least one electrical component after initiating each pulse of the at least one distendable element.

19. The method of claim 17, further comprising:
    initiating each pulse of the at least one electrical component after an occurrence of a waveform of the sensed myoelectrical activity; and
    initiating each pulse of the at least one distendable element after initiating each pulse of the at least one electrical component.

20. The method of claim 17, further comprising:
    synchronizing the each pulse of the at least one electrical component with the each pulse of the at least one distendable element.

21. The method of claim 17, further comprising:
    initiating each pulse of the at least one distendable element at a select frequency during disorganized myoelectrical activity; and
    initiating each pulse of the at least one electrical component after initiating the each pulse of the at least one distendable element.

22. The method of claim 17, further comprising:
    initiating each pulse of the at least one electrical component at a select frequency during disorganized myoelectrical activity; and
    initiating each pulse of the at least one distendable element after initiating each pulse of the at least one electrical component.

23. The method of claim 17, further comprising randomly pulsing the at least one distendable element and randomly pulsing the at least one electrical component during normal myoelectrical activity.

24. The method of claim 16, further comprising administrating a hormonal stimulant through one of the lumens in the tube to an outlet at a location in the compartment.

25. A device for stimulating select body tissues and organs from within a compartment in a body, the device comprising:
    a multi-lumen tube positionable in the compartment of the body and having a proximal end and a distal end; and
    a first active portion located along the tube between the proximal and distal ends and positioned proximate to a first portion of the compartment of the body, the first active portion configured to repeatedly provide a sequence of pulses of mechanical distension and a sequence of pulses of electrical stimulation to the first portion of the compartment of the body over a period of time.

26. The device of claim 25, further comprising a second active portion located along the tube between the first active portion and the distal end and positioned proximate to a second portion of the compartment of the body, the second active portion configured to repeatedly provide a sequence of pulses of mechanical distension and a sequence of pulses of electrical stimulation to the second portion of the compartment of the body for the period of time.

* * * * *